US012138051B2

(12) United States Patent
Burman et al.

(10) Patent No.: US 12,138,051 B2
(45) Date of Patent: Nov. 12, 2024

(54) CALIBRATION SYSTEM AND METHOD FOR SPECTROSCOPIC DEVICES

(71) Applicant: RCE Technologies, Inc., Carlsbad, CA (US)

(72) Inventors: Atandra Burman, Bermuda Dunes, CA (US); Jitto Titus, Acworth, GA (US); Siddharth Biswal, Atlanta, GA (US)

(73) Assignee: RCE Technologies, Inc, Carlsbad, CA (US)

( * ) Notice: Subject to any disclaimer, the term of this patent is extended or adjusted under 35 U.S.C. 154(b) by 0 days.

(21) Appl. No.: 18/625,438

(22) Filed: Apr. 3, 2024

(65) Prior Publication Data

US 2024/0252075 A1 Aug. 1, 2024

Related U.S. Application Data

(63) Continuation of application No. PCT/US2022/046281, filed on Oct. 11, 2022.

(60) Provisional application No. 63/254,248, filed on Oct. 11, 2021.

(51) Int. Cl.
*A61B 5/1495* (2006.01)
*A61B 5/145* (2006.01)
*A61B 5/1455* (2006.01)
*G16H 40/40* (2018.01)

(52) U.S. Cl.
CPC ........ *A61B 5/1495* (2013.01); *A61B 5/14546* (2013.01); *A61B 5/1455* (2013.01); *G16H 40/40* (2018.01); *A61B 2560/0238* (2013.01)

(58) Field of Classification Search
CPC . A61B 5/1455; A61B 5/14546; A61B 5/1495; A61B 2560/0238
See application file for complete search history.

(56) References Cited

U.S. PATENT DOCUMENTS

| | | | |
|---|---|---|---|
| 7,215,982 B2* | 5/2007 | Oshima | A61B 5/1495 600/316 |
| 8,148,691 B1 | 4/2012 | Wong | |
| 2003/0031597 A1* | 2/2003 | Sota | A61B 5/1455 600/316 |
| 2003/0114738 A1 | 6/2003 | Zonios et al. | |
| 2004/0186382 A1 | 9/2004 | Modell | |
| 2005/0171413 A1* | 8/2005 | Blair | A61B 5/1455 600/310 |

(Continued)

OTHER PUBLICATIONS

International Search report for International Application No. PCT/US2022/046281, dated Mar. 2, 2023.

*Primary Examiner* — Eric F Winakur
(74) *Attorney, Agent, or Firm* — Quinn IP Law

(57) ABSTRACT

Transdermal optical sensing systems and methods of use and calibration are described. The systems include a master and secondary sensing device, an optical component arranged within the device, with an optical component surface exposed for contact with an epidermis of a subject, an optical emitter, an optical detector, and electronics including a controller configured to measure the light at the optical detector to determine the presence of one or more compounds within the epidermis, to perform a calibration of the sensing device including generating a master calibration curve, to detect a condition state of the sensing device, and to generate a biomarker correlation curve for a biomarker or combination of biomarkers.

29 Claims, 11 Drawing Sheets

(56) References Cited

U.S. PATENT DOCUMENTS

2008/0309922 A1\* 12/2008 Anders ................ G01N 21/552
  356/73
2017/0138843 A1\* 5/2017 Koop ................... G01N 21/278
2020/0390365 A1 12/2020 Labelle et al.

\* cited by examiner

CALIBRATION SYSTEM AND METHOD FOR SPECTROSCOPIC DEVICES

CROSS-REFERENCE TO RELATED APPLICATIONS

This application claims the benefit of International Application Serial No. PCT/US2022/046281 which claims the benefit of U.S. Provisional Application 63/254,248 filed Oct. 11, 2021, the contents of each of which are hereby incorporated by reference in its entirety.

TECHNICAL FIELD

The subject matter disclosed herein generally relates to medical diagnostic devices and methods and, more particularly, to transdermal patient assessment and diagnostic devices and methods and calibration thereof.

BACKGROUND

Over ten million symptomatic patients present with chest pain in emergency departments in the United States each year. Over 80% of these are due to non-cardiac causes, resulting in an unnecessary burden in the emergency departments. This reveals a need for non-invasive detection techniques that can streamline the emergency department workflows, preferably with a rapid testing mechanism for timely analysis. Furthermore, one out of five myocardial infarctions is asymptomatic (silent), leading to nearly 200,000 silent myocardial infarctions each year in the US. Therefore, the development of new technologies that can allow early non-invasive detection of myocardial injury is imperative.

State-of-the-art for troponin assays involve the use of two or more antibodies, one of which is labeled, typically with a chemiluminescent tag, which add another level of complexity in the analysis. While recent point-of-care (POC) solutions have reduced the time required to obtain test results, there still remains a dependency upon blood draws coupled with lower analytical sensitivity compared to central laboratory testing. This has resulted in limited application of such solutions toward effective discharge from emergency departments. Accordingly, improved solutions are desired to improve emergency room discharge and patient diagnostics and evaluation.

SUMMARY

According to embodiments of the present disclosure, calibration techniques and methods are described for spectroscopic sensors, such as optical sensing systems. In a non-limiting example, systems and methods for the calibration of transdermal optical sensing systems is disclosed herein. In accordance with some embodiments, a master device is calibrated using the techniques described herein, and then subsequent devices are conformed to the master device through an electronic calibration process, such that no physical calibration sample is required to calibrate the subsequent devices to the master device. As such, all devices may be aligned such that readings and/or output thereof is uniform and accurate.

A method of calibrating an optical sensing device is disclosed herein. In an illustrative example, the optical sensing device includes an emitter, a detector, and an optical component coupled to the emitter and the detector. The optical sensing device further including a power source and electronics including a controller. The method includes isolating the optical component from an external environment, applying a plurality of voltages to the emitter, detecting, via the detector, an output corresponding to each voltage, and recording each voltage paired with the corresponding output to a baseline dataset. The plurality of voltages includes an initial voltage, a final voltage, and incremental voltages stepped by a voltage increment between the initial voltage and the final voltage; and generating, using the baseline dataset, a calibration curve.

In one example, the optical sensing device is a master optical sensing device and the calibration curve is a master calibration curve, and the method of calibrating subsequent devices, also referred to herein as secondary devices, includes providing a secondary optical device including a secondary emitter, a secondary detector, a secondary optical component, a power source and electronics including a secondary controller. The method further includes calibrating the secondary optical device by: isolating the secondary optical component from the external environment, applying the plurality of voltages to the secondary emitter, detecting, via the secondary detector, an output corresponding to each of the voltages, and recording the outputs to a secondary dataset. The method continues with generating a secondary calibration curve by: generating an unadjusted calibration curve based on the secondary dataset, and adjusting, using a calibration model, the unadjusted calibration curve to align with the master calibration curve.

In one example, the method can include analyzing the unadjusted calibration curve to determine a condition state of the secondary optical device, where the condition state corresponds to at least one of a damaged condition, a malfunctioning conditioning, a misaligned condition, or a wear condition of the secondary optical device. Analyzing the unadjusted calibration curve can include at least one of: comparing the unadjusted calibration curve to the master calibration curve; and comparing the unadjusted calibration curve to the secondary calibration curve.

In one example, the optical sensing device is operable as a transdermal optical sensing device for monitoring at least one biomarker in a subject, with the method further including generating a biomarker correlation curve for the at least one biomarker. Generating the biomarker correlation curve includes, for each subject of a plurality of subjects, recording a detector output from the optical sensing device in contact with the subject; wherein the detector output corresponds to a predetermined operating voltage of the emitter, and obtaining a corresponding laboratory value of the at least one biomarker of the subject. The method continues with correlating, using the detector output and the corresponding laboratory value of the at least one biomarker obtained from the plurality of subjects, the detector output to the values of the at least one biomarker, where the biomarker correlation curve correlates the detector output to a value of the at least one biomarker.

A system for calibration of an optical sensing device is disclosed herein. The system includes a master optical sensing device including an emitter, a detector, and an optical component coupled to the emitter and the detector, the optical sensing device further including a power source and electronics including a controller. The controller of the master optical sensing device is configured to apply a plurality of voltages to the emitter, and to detect, via the detector, an output corresponding to each voltage. The controller is configured to record each voltage paired with the corresponding output to a baseline dataset, where the plurality of voltages includes an initial voltage, a final voltage, and incremental voltages stepped by a voltage increment between the initial voltage and the final voltage. The controller is further configured to generate, using the baseline dataset, a master calibration curve. The system further includes a secondary optical sensing device including an emitter, a detector, and an optical component coupled to the emitter and the detector, the secondary optical sensing device further including a power source and electronics including a controller, where the controller of the secondary optical sensing device is configured to apply the plurality of voltages to the emitter, and detect, via the detector, an output corresponding to each voltage. The controller is configured to record each voltage paired with the corresponding output to a secondary dataset, and to generate, using the secondary dataset, an unadjusted calibration curve. The secondary optical sensing device is configured to receive, from the master optical sensing device or the external component, a calibration model including the master calibration curve, and the controller is configured to generate a secondary calibration curve using the calibration model. Advantageously, the calibration process for the secondary optical sensing device is an electronic process, e.g., a physical sample or physical master is not required to calibrate the secondary device.

A method of calibrating an optical sensing device of a transdermal optical sensing system is disclosed herein, where the transdermal optical sensing system is operable for monitoring at least one biomarker in a subject. In an illustrative example, the system includes a master optical sensing device and a secondary optical sensing device, and the method of calibrating includes generating, using the master optical sensing device, a master calibration curve, generating, using the secondary optical sensing device, an unadjusted calibration curve, generating, using the unadjusted calibration curve and the master calibration curve, a secondary calibration curve, and calibrating the secondary optical sensing device to the master optical sensing device using the secondary calibration curve. Advantageously, the method disclosed herein provides accurate and consistent calibration of the secondary optical sensing device to the master optical sensing device without having to provide or use a physical sample or physical master to calibrate the secondary device.

The foregoing features and elements may be combined in various combinations without exclusivity, unless expressly indicated otherwise. These features and elements as well as the operation thereof will become more apparent in light of the following description and the accompanying drawings. It should be understood, however, that the following description and drawings are intended to be illustrative and explanatory in nature and non-limiting.

BRIEF DESCRIPTION OF THE DRAWINGS

The subject matter is particularly pointed out and distinctly claimed at the conclusion of the specification. The foregoing and other features, and advantages of the present disclosure are apparent from the following detailed description taken in conjunction with the accompanying drawings in which:

DETAILED DESCRIPTION

Figures 1A, 1B:
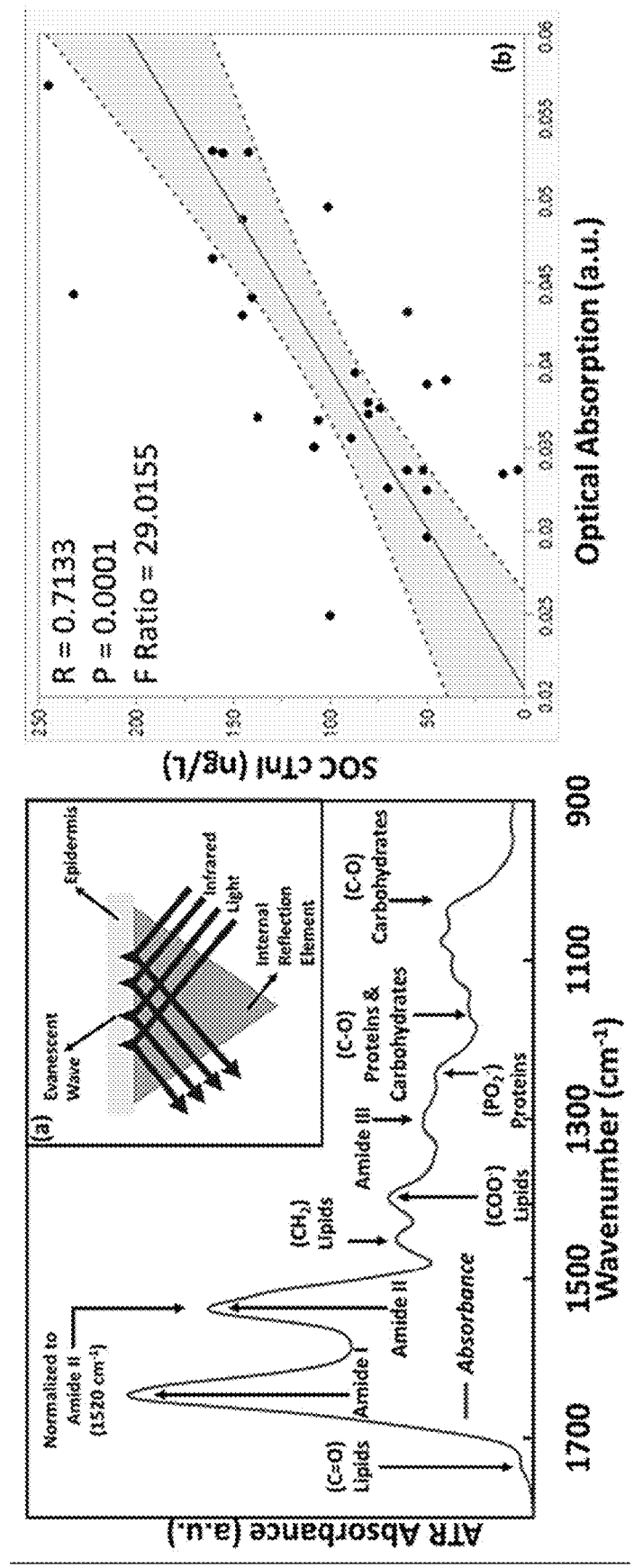
FIG. 1A is a schematic plot of characteristic peaks representative of individual molecular components, with the inset illustration of FIG. 1A illustrating a working principle of attenuated total reflectance in accordance with an embodiment of the present disclosure.
FIG. 1B illustrates a linear correlation between high sensitivity cTnI assay-derived data and the optical device absorption in accordance with an embodiment of the present disclosure.

Patient diagnostics may require complex testing and/or analysis. For example, the diagnosis of acute coronary syndrome (ACS), principally requires the monitoring of surface electrocardiograms and cardiac injury biomarkers within the clinical context. However, conventionally used biomarkers like cardiac troponins require invasive blood draws that can only be done periodically for the evaluation of ACS patients. Embodiments of the present disclosure are directed to transdermal monitoring of cardiac troponin-I (cTnI) to detect elevated states of the chemical. This may be achieved through use of non-invasive detection of cTnI-dependent infrared absorption. Using stepwise laboratory, benchtop, and clinical studies it has been determined there is a significant correlation between optically-derived data and blood-based immunoassay measurements. These data establish the potential of embodiments of the present disclosure for improving point-of-care risk stratification.

As noted above, many symptomatic patients present with chest pain in emergency departments in the United States each year, with over 80% of these due to non-cardiac causes. This results in an unnecessary burden upon emergency departments, hospitals, and other healthcare institutions. Embodiments of the present disclosure may provide for an instant, non-invasive detection technique that can streamline patient care in such symptomatic patients. Furthermore, as noted a significant percentage of myocardial infarctions are asymptomatic (e.g., silent). Embodiments of the present disclosure may provide for early non-invasive detection of myocardial injury.

State-of-the-art for troponin assays involve use of two or more antibodies, one of which is labeled, typically with a chemiluminescent tag. This tagging and process can add additional levels of complexity in analysis and diagnostic procedures. While recent point-of-care (POC) solutions may reduce time to test results, there still remains a dependency upon blood draw from a patient coupled with lower analytical sensitivity compared to central laboratory testing. As such, these in-field applications (e.g., at an emergency department) may be limited in their application toward effective patient discharge.

Embodiments of the present disclosure are directed to solutions employing infrared spectroscopy. Infrared spectroscopy provides a characterization technique from the ability to probe into a material at a molecular level. This molecular level probing can provide for an inherently sensitive mode of interrogation. Advantageously, by employing such techniques, minimal or no sample preparation may be required (and no blood draws or the like are required). That is, similar to pulse oximeters, breathalyzers, and bilirubinometers, a sample is not taken from the body of a patient in the non-invasive procedures described herein.

Infrared spectroscopy has some drawbacks which have limited the application in point of care and diagnostic processes with a patient, for example, in an emergency room. Firstly, signal-to-noise ratios strongly dictate the minimum detectable limit, and thus may bound the applicability for in situ applications (e.g., no clinic/lab controls). Secondly, because all matter is a source of infrared radiation, efficiencies of IR-based devices can be confounded by stray (e.g., ambient) light. Finally, the most sensitive mode of operation (which is Fourier Transform IR spectroscopy) requires a large footprint and is highly sensitive to mechanical vibrations, due to moving components. As such, the most sensitive application is often confined to ex vivo modalities (e.g., not directly at the patient). Embodiments of the present disclosure may provide for solutions that may mitigate or entirely eliminate the above mentioned challenges, in addition to providing other advantages and improvements in the field of patient diagnostics. In view of this, embodiments of the present disclosure are directed to an efficacious, non-invasive device capable of risk-stratifying patients based on IR detected chemicals. In some non-limiting embodiments, the devices disclosed herein may enable efficacious, non-invasive devices capable of risk-stratifying ACS patients based on Troponin-I levels.

Absorption spectroscopy is a molecular characterization technique typically used to study the composition of materials and thereby determine concentrations of the substance of interest in a native state. When infrared radiation is incident on a material such that the energy is equivalent to the chemical bond vibrational mode of the material, there is energy transfer causing the absorption of the light radiation leading to an active vibrational mode. This results in certain energies or wavelengths of light being absorbed by the material that are unique to the material. Thus, the material can be compositionally characterized by performing a differential measurement of the light before and after it passes through the material.

Traditional configurations of absorption spectroscopy involve directing infrared radiation through a sample to be measured and detecting the light on the opposite side using a thermal or optical detector. This restricts the mode of interrogation to in vitro or ex vivo measurement. To overcome this issue, embodiments of the present disclosure are directed to employing an Attenuated Total Reflectance (ATR) configuration. In ATR configurations of the present disclosure, light is totally internally reflected inside an optical component, such as an internal reflection element or prism, of a higher refractive index than the material to be characterized (e.g., blood). Photons come out of the surface of the crystal penetrating the sample (e.g., skin) and then are coupled back into the system. This partially penetrated evanescent wave can interact with the material on the surface of the crystal, affording the intensities of the frequencies of light measured after passing through the prism to be highly sensitive to the materials present on the surface of the crystal. The penetration depth of the photons is a function of the wavelength of light and the refractive indices of the internal reflection element crystal and sample. In the optical sensor/detector design of embodiments of the present disclosure, mid-infrared radiation is introduced into an internal reflection element. Such internal reflection elements, in accordance with embodiments of the disclosure and as example only, may be germanium, zinc sulfide crystals. After the infrared light totally internally reflects at a contact surface of the internal reflection element, the infrared light may be detected by an infrared detector. In accordance with some embodiments, the signals before and after the internal reflection element makes contact with the sample are differentially processed to obtain optical characteristics of the sample.

Referring now to FIGS. 1A-1B, schematic plots of various vibrational modes observed when mid-infrared light (MIR) interacts with the epidermis of a patient in an Attenuated Total Reflectance (ATR) configuration are shown. FIG. 1A indicates the characteristic peaks representative of individual molecular components, the inset illustration of FIG. 1A illustrates the working principle of Attenuated Total Reflectance. FIG. 1B illustrates a linear correlation of 71% was observed between the high sensitivity cTnI assay-derived data and the optical device absorption (n=30).

In the plot of FIG. 1A, the vertical axis is an absorbance (ATR) in absorbance units (a.u.) and the horizontal axis is wavenumber in reciprocal centimeter ($cm^{-1}$). In the plot of FIG. 1B, the vertical axis is cTnI (Fhigh sensitivity cardiac troponin-I assay (hs-cTnI)) in nanogram per liter (ng/L) and the horizontal axis is optical absorption in absorbance units (a.u.), R refers to the linear coefficient of correlation and P is the p-value associated with the correlation, and a higher F-ratio indicates the degree of deviation from the null hypothesis.

As shown in FIG. 1A, peaks representative of specific chemical compositions may be obtained through a device configured to perform Attenuated Total Reflectance upon a surface (e.g., epidermis of a patient). As shown in the insert of FIG. 1A, infrared light is passed into and through an internal reflection element that is arranged in contact with the epidermis. The infrared light will internally reflect within the interior reflection element and the reflected infrared light may be monitored to obtain the peak data illustrated in FIG. 1A. As shown, an evanescent wave may penetrate into the epidermis.

An investigational study was conducted to determine the spectral features that are unique to cardiac markers such as cardiac Troponin I, creatine kinase-MB, and B-type natriuretic peptide (BNP), with the optical characterization of these substances in their pure form. This measurement was carried out using an infrared spectrometer employing a diamond IRE, to identify a unique concert of absorption features that can be deemed as a signature for cardiac troponin. This allows one to optically detect and quantify the presence of that particular biomarker in a host substrate such as whole blood. De-identified healthy whole blood was procured and characterized to determine if there are any confounding overlaps in the absorption peaks of blood and cardiac biomarkers. Consequently, to confirm the efficacy of ATR mode of interrogation, a number of de-identified blood samples with the corresponding measurement of high sensitivity cardiac troponin values were procured. Patients were identified with a spectrum of Troponin-I values between the limits of detection of the assay namely, a cardiac troponin-I assay (e.g., hs-cTnI). The blood samples were then optically characterized ex vivo with the modality of total internal reflection using a research-grade benchtop Fourier Transform infrared spectrometer employing a diamond IRE. Each blood sample to be characterized was one microliter in volume as deposited on the IRE. Each sample was measured in triplicate, with every repeat being an average of 32 co-added scans at a resolution of 4 $cm^{-1}$. The optical readouts were investigated for correlation (as illustrated in FIG. 1B) with that of cTnI concentrations. A positive linear correlation of 71% (p=0.0001) was observed between optical and troponin-I data within the range of 2.5 to 250 ng/L.

Embodiments of the present disclosure are directed to ambulatory, non-invasive transdermal wearable devices. The wearable devices may be installed on the wrist of a patient or arranged in contact with the skin of a patient (e.g., at locations other than the wrist).

Figure 2A:
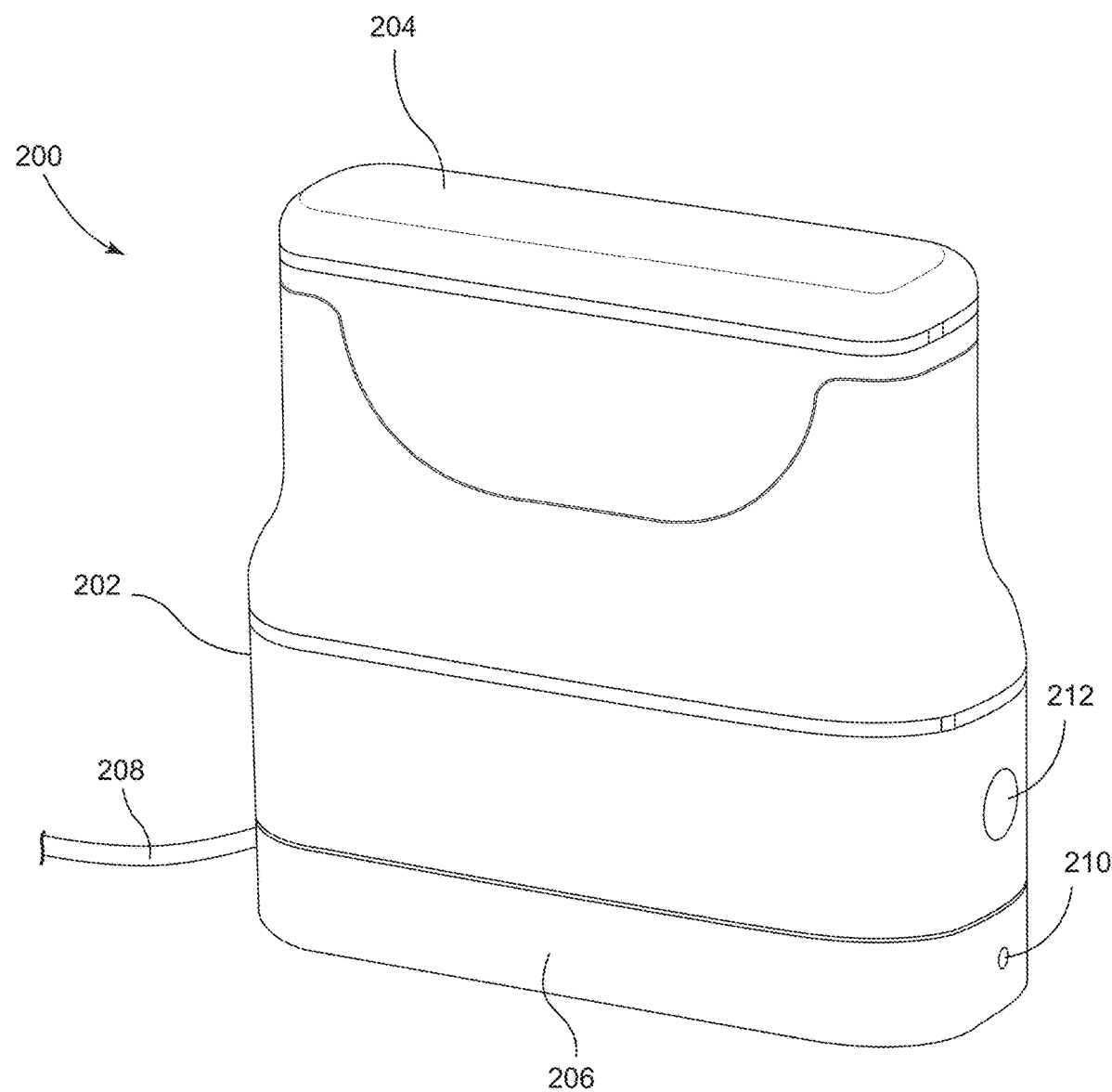
FIG. 2A is a schematic illustration of a transdermal optical sensing system in accordance with an embodiment of the present disclosure.
Figure 2B:
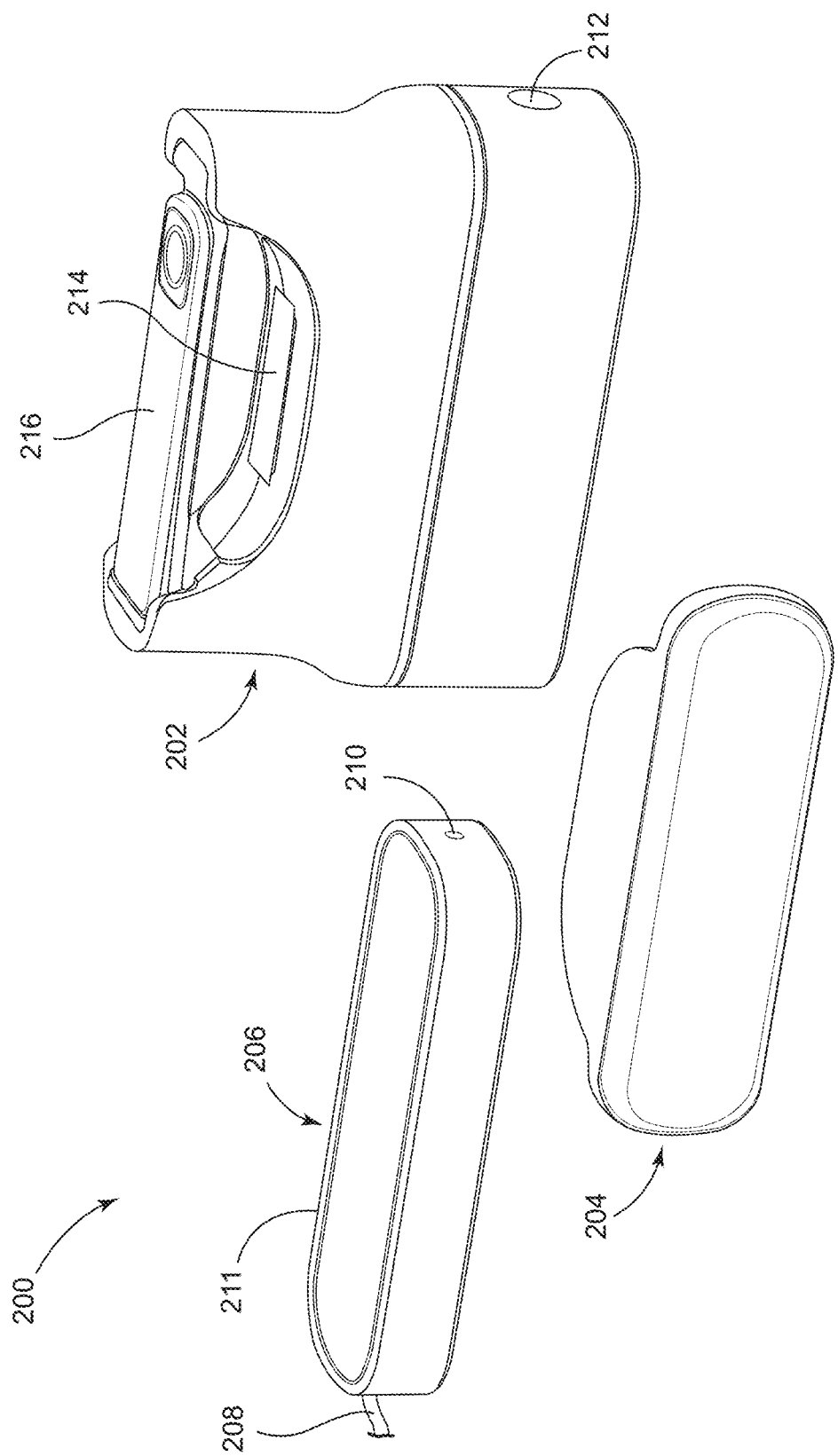
FIG. 2B illustrates components of the transdermal optical sensing system of FIG. 2A as separated from each other.

Referring now to FIGS. 2A-2B, schematic illustrations of a transdermal optical sensing system 200 in accordance with an embodiment of the present disclosure are shown. FIG. 2A illustrates the transdermal optical sensing system 200 as assembled and FIG. 2B illustrates the transdermal optical sensing system 200 with the components thereof separated. The transdermal optical sensing system 200 includes a main body 202, cover 204, and a base 206. The main body 202 may be configured as a housing or enclosing structure configured to house electrical and optical components therein, as described below. The cover 204 is configured to removably cover a portion of the main body 202 and may be attachable to the main body 202 by snap engagement, sliding fit, or otherwise, as will be appreciated by those of skill in the art. The cover 204 may be configured to provide a sealing cover of components of the main body 202.

The base 206, in this embodiment, is configured to enable charging of electrical components of the main body 202. As shown, the base 206 includes a power cable 208 that may be plugged into a power source, such as a wall outlet, a charged-USB port, a battery, or the like. In some embodiments, the base 206 may be configured to provide wireless charging to electrical components within the main body 202. In other embodiments, an electrical port connection (e.g., USB, pin-connection, etc.) may be provided to enable physical electrical connection between the base 206 and the main body 202. In this configuration, the base 206 also includes an optional indicator light 210. The indicator light 210 may be provided to indicate a charging state or other operational state of the electronics of the main body 202 and/or of the transdermal optical sensing system 200. The base 206 may also have a lip 211 or other structural feature (e.g., protrusion, rim, etc.) that is configured to enable proper positioning and alignment of the main body 202 on the base 206, such as for the purpose of charging and/or data transmission. In some embodiments, rather than the lip 211 around a periphery of the base 206, or in combination therewith, a central feature, such as a protrusion or depression may be used that mates with a companion feature (e.g., depression or protrusion) of the main body 202.

The main body 202, in this illustrative embodiment, includes an operational button 212. The operational button 212 may be configured to enable powering the electronics of the main body 202 on and off. Further, in some embodiments, the operational button 212 may be configured to enable use of the transdermal optical sensing system 200 (e.g., to perform a diagnostic operation as described herein). In some embodiments that have a single operational button 212, the single operational button 212 may be configured to have different actuation mechanisms to achieve different operational states. For example, a long press may be configured for powering on or off the transdermal optical sensing system 200. A single press or a multi-press may enable operation of the transdermal optical sensing system 200 to perform a diagnostic operation. In other embodiments, multiple operational buttons may be configured on main body 202 for performing different functions. Further still, in some embodiments, the operational button 212 may be omitted, and the transdermal optical sensing system 200 may be configured to be controlled or operated by a remote device (e.g., remote controller, mobile device, computer, smart phone, etc.). It will be appreciated that various different control and/or power button options are possible without departing from the scope of the present disclosure.

FIG. 2B illustrates the transdermal optical sensing system 200 with the base 206 and the cover 204 separated from the main body 202. As shown, the main body 202 includes an internal reflection element 214 (also referred to as IRE 214) and a retention member 216. The IRE 214 may be an internal reflection element, such as a prism, crystal, or the like, as described above. The IRE 214 is positioned and arranged within the main body 202 such that a portion of the IRE 214 is exposed. The IRE 214 may be optically coupled to an optical source and an optical detector (e.g., both IR wavelength source/detector) that are arranged within the main body 202. The exposed portion of the IRE 214 is arranged such that the wrist or other part of a patient's body may be arranged in contact with the IRE 214. The main body 202 may be shaped and contoured to aid in ensuring that appropriate contact between the epidermis of a patient remains in contact with the IRE 214 when performing a diagnostic operation. The retention member 216 is an optional element and can be provided to further aid in ensuring contact between epidermis and the IRE 214.

The retention member 216 may be a strap, band or other structure that can partially wrap about a patient's wrist and retain the wrist in a position of constant contact with the IRE 214. The retention member 216 can include securing means, such as a buckle, pin-and-hole connection, hook-and-loop connection, snap-buttons, magnetic clasp, a tie strap, or the like, as will be appreciated by those of skill in the art. In some embodiments, a strap or other band may be housed or retained within the main body 202, and may be wound or tensions (e.g., like a seatbelt) and may be configured for auto-tensioning once a wrist is placed on the transdermal optical sensing system 200.

The transdermal optical sensing system 200 may be a portable or semi-portable device. In some embodiments, the transdermal optical sensing system 200 may be a desktop or tabletop device, that can be moved around from place to place. In some embodiments, the transdermal optical sensing system 200 may be configured and sized for bedside use, and thus has a relatively small form factor that can fit on a hospital bed, or the like, with a patient and not disrupt such patient.

Figure 3:
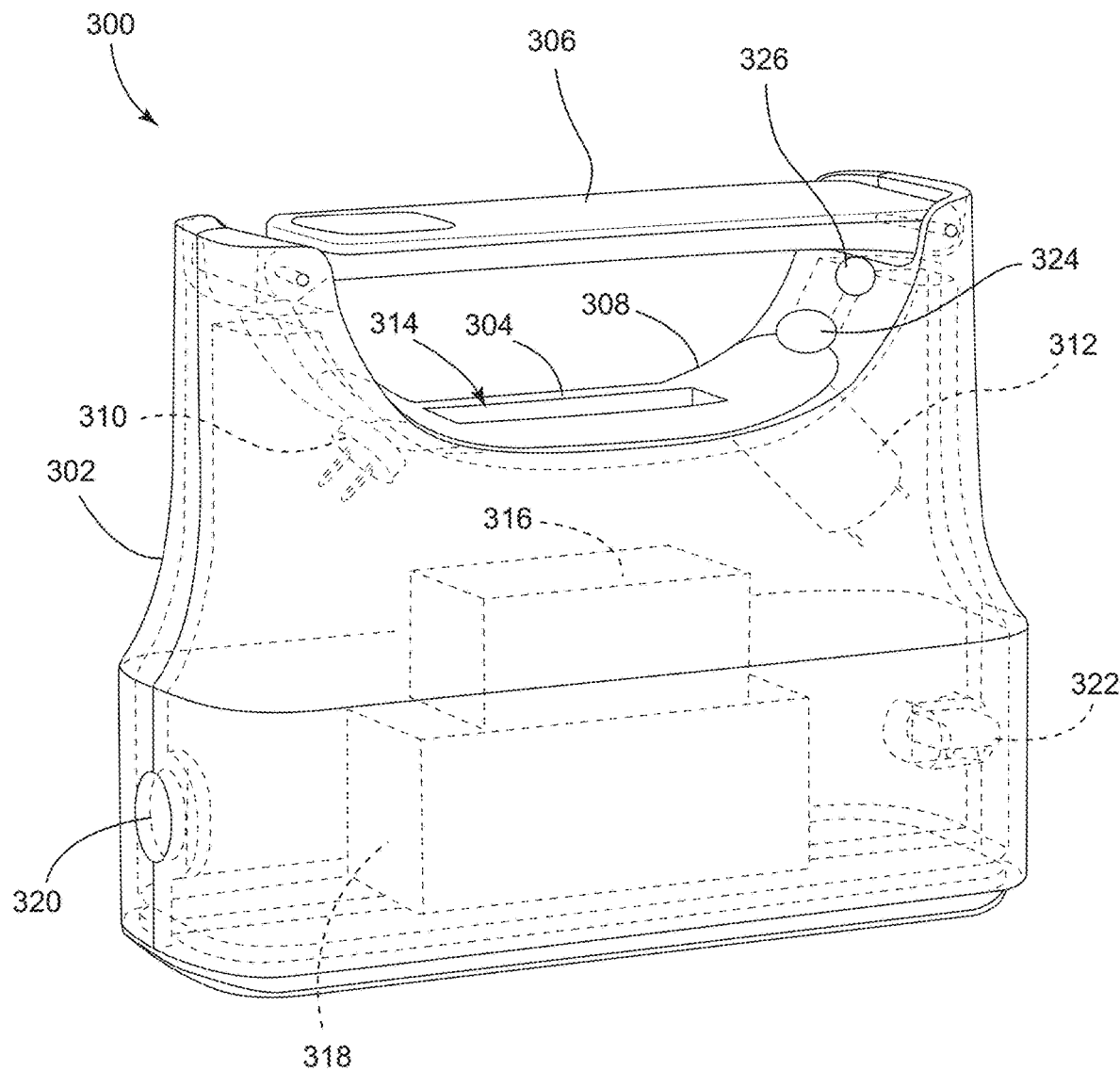
FIG. 3 is a schematic illustration of a transdermal optical sensing system in accordance with the present disclosure.

Turning now to FIG. 3, a schematic illustration of a transdermal optical sensing system 300 in accordance with an embodiment of the present disclosure is shown. The transdermal optical sensing system 300 is similar to that in configuration as the transdermal optical sensing system 200 of FIGS. 2A-2B. In the illustration of FIG. 3, the transdermal optical sensing system 300 is not shown with a cover or base, as described above, but can be configured to include such elements.

The transdermal optical sensing system 300 includes a main body 302 that houses internal electronics and defines a slot or area for a patient to put their epidermis in contact with an IRE. As shown, the transdermal optical sensing system 300 includes an IRE 304 and a retention member 306 for holding a patient's wrist in contact with the IRE 304. The IRE 304 may be surrounded by a band 308. The band 308 may be a soft or pliable material to aid in comfort to a patient. Further, the material of the band 308 may be selected to compress when a wrist is resting thereon, and thus the epidermis of the patient may contact the IRE 304. For example, the band may be formed of rubber or the like. The band 308 may prevent debris or particulates from entering into the main body 302.

The IRE 304 is optically coupled to an optical source 310 and an optical receiver 312. The optical source 310 is an electronic element that is configured to generate one or more wavelengths of light to be projected into the IRE 304. In some embodiments, the wavelength(s) of light generated by the optical source 310 may be within the infrared optical band. The optical source 310 may be a 2-channel optical source, a 4-channel optical source, a multichannel optical source, or the like. It will be appreciated that any number of channels, including a single channel, may be used, without departing from the scope of the present disclosure. The incident light is directed to an IRE surface 314 of the IRE 304. When a patient has placed their epidermis in contact with the IRE 304, the incident light will contact and interact with the epidermis at the IRE surface 314. After interaction with the epidermis at the IRE surface 314, the light will internally reflect within the IRE 304 and the reflected light may be detected by the optical receiver 312. The optical receiver 312 may be configured to detect the wavelength, amplitude, or other characteristics of the reflected light.

The transdermal optical sensing system 300 includes internal electronics including, at least, a controller 316 and a power source 318. The power source 318 is configured to supply electrical power to, at least, the controller 316, the optical source 310, and the optical receiver 312. The controller 316 may be operably coupled to each of the optical source 310 and the optical receiver 312. Such operably coupling may be by electrical wires or by wireless connection. The controller 316 may be configured to cause light generation at the optical source 310. Further, the controller 316 may be configured to receive data or information from the optical receiver 312 in order to perform analysis thereon. In some embodiments, the controller 316 may be configured to transmit data received from the optical receiver 312 to an external component, such as a smart phone, a mobile device, a computer, a cloud network, etc. In some such embodiments, processing and analysis of the information or data detected at the optical receiver 312 may be processed for diagnostic purposes at the remote component. In other embodiments, the processing may be performed at the controller 316. The transdermal optical sensing system 300 also includes an operational button 320 and an indicator light 322 that may be configured similar to that described above.

The controller 316 is configured to process the electrical data extracted from the detector (optical receiver 312) and emitter (optical source 310). The processing involves a differential between the "on" and "off" state of the optical source 310 to remove the effects of ambient conditions. Further, in accordance with some embodiments, four channels of data extracted from the optical receiver 312 may be differentially processed with one channel always being used as a reference, allowing for standardization. For example, in some such embodiments, a first channel may be used for calibration, normalization, and/or reference of the other three channels. In other embodiments, a two channel system may be used, or a multichannel system, where a scan is performed through a range continuously or incrementally. Further, in some embodiments, a single channel configuration may be employed. Patient data may also be weighted by the background data in order to obtain absolute values. Finally, the controller 316 is configured to output a troponin value on a display (e.g., on the optical sensing system and/or on a remote display or portal).

In some embodiments, the transdermal optical sensing system 300 can include additional sensors or detectors. For example, an EKG sensor 324 may be provided on or near the band 308 and positioned such that when a user or patient places their wrist on the transdermal optical sensing system 300, the wrist will contact the IRE surface 314 of the IRE 304 and the EKG sensor 324. The EKG sensor 324 may include one or more contact points (e.g., two) for ensuring detection of heart rate during a measurement taken by the transdermal optical sensing system 300. As such, biomarker data and heart rate data may be obtained and collected simultaneously. Advantageously, such data collection can enable improved health monitoring by correlating various types of data of the patient. The example is non-limiting and illustrative, such that other physiological states of the subject and/or combination of biomarkers and health indicators could be monitored using the transdermal optical sensing system 300, by incorporation of additional sensors or detectors and/or calibration of the sensing device 200 to detect a plurality of biomarkers. The EKG sensor 324 may be an electrical component that is electrically connected to and controller by the controller 316. The transdermal optical sensing system 300 may also include one or more detection sensors 326. The detection sensor 326 may be an optical or other type of proximity sensor and/or may be a pressure sensor. The detection sensor 326 may be connected to the controller 316 and can enable proper detection and measurements. For example, the controller 316 may be configured to perform a measurement operation only when the detection sensor 326 detects the presence of a wrist (or other body part) positioned on the transdermal optical sensing system 300.

Figure 4A:
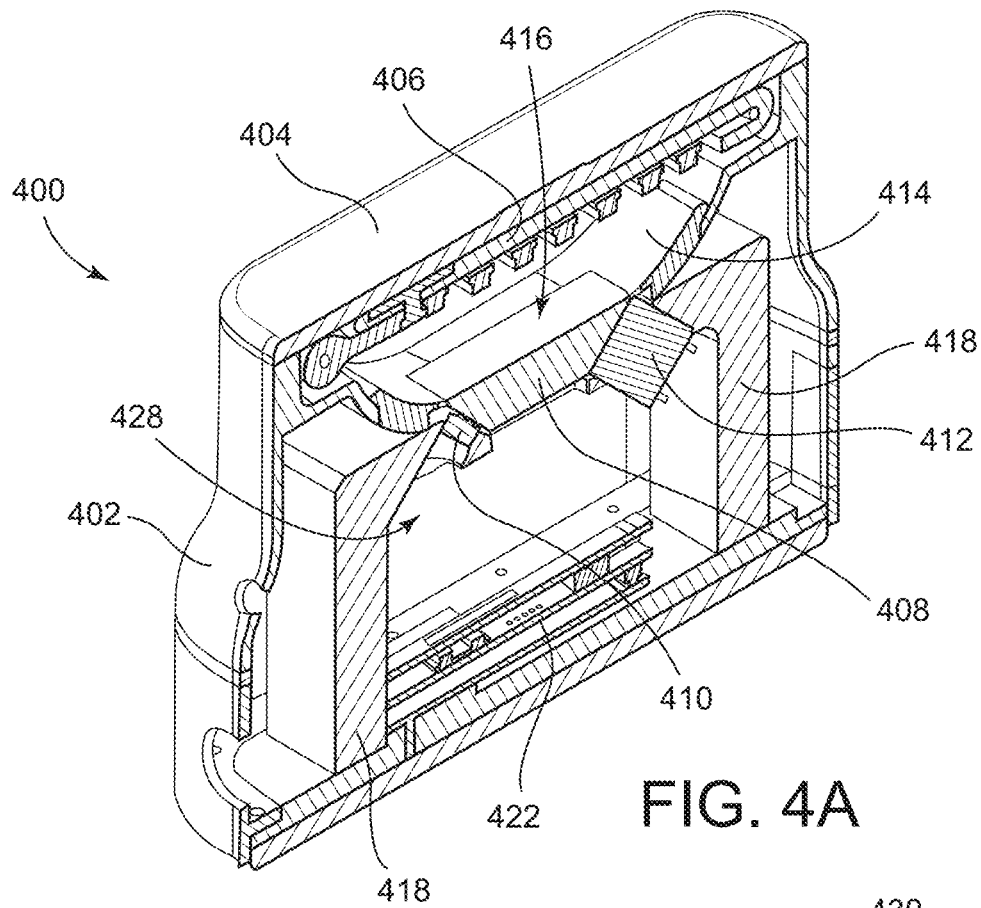
FIG. 4A is a cross-sectional illustration of a transdermal optical sensing system in accordance with an embodiment of the present disclosure.
Figure 4B:
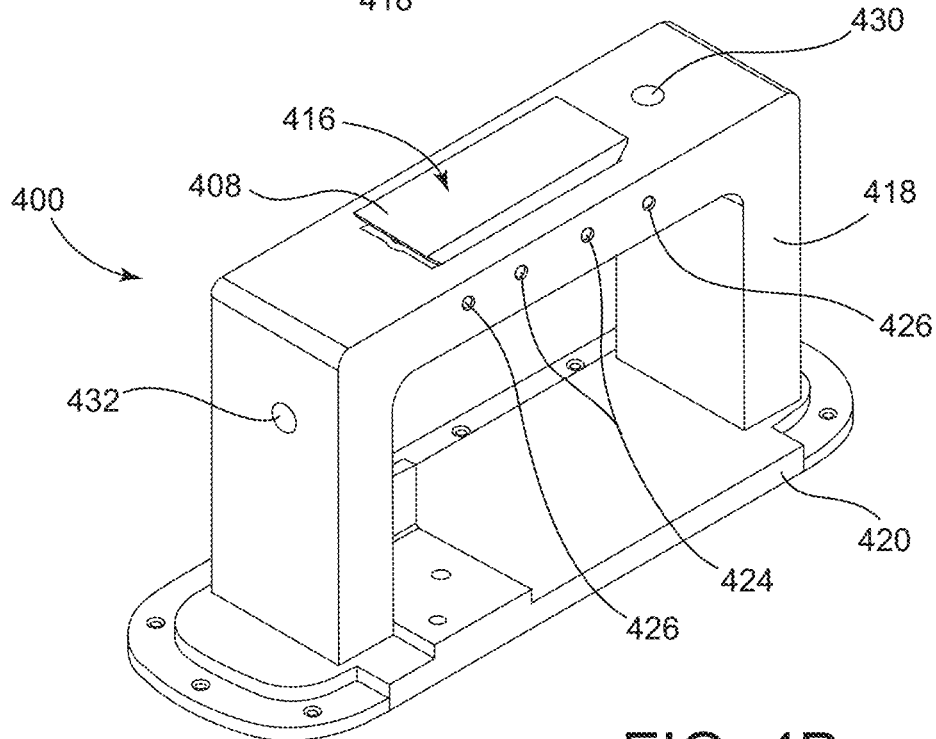
FIG. 4B is a schematic illustration of components of the transdermal optical sensing system of FIG. 4A.

Turning now to FIGS. 4A-4B, schematic illustrations of a transdermal optical sensing system 400 in accordance with an embodiment of the present disclosure are shown. FIG. 4A illustrates a cross-sectional view of the transdermal optical sensing system 400 and FIG. 4B illustrates a structural arrangement of components of the transdermal optical sensing system 400. The transdermal optical sensing system 400 may be similar to that shown and described above.

The transdermal optical sensing system 400 includes a main body 402 with a cover 404 removably attached thereto. A retention member 406 is attached to the main body 402, similar to that described above. The transdermal optical sensing system 400 includes an IRE 408 with associated optical source 410 and optical detector 412. A band 414 is arranged about an IRE surface 416, similar to that described above.

Within the main body 402 of the transdermal optical sensing system 400, a structural frame 418 is provided to support the IRE 408 and components associated therewith.

The structural frame 418 may extend upward from a structural base 420 which is configured to be affixed within the main body 402 and support the structural frame 418. The structural frame 418 may be configured to dissipate force away from electrical components 422 of the transdermal optical sensing system 400. Further, the structural frame 418 may enable isolating of the optical elements from mechanical vibrations and/or provide for heat dissipation through the material selection of the structural frame 418. The structural base 420 may be configured to house and/or support the electronic components 422 and/or power components (not shown for clarity). The electronic components 422 can include processors, input/output elements, power control circuits, and/or other printed circuit boards or the like, as will be appreciated by those of skill in the art. The power components can include batteries and/or hardwired electrical power components (e.g., wireless charging elements, ports, power cable, etc.).

In accordance with some embodiments of the present disclosure, and as shown in FIG. 4B, the IRE 408 may be mounted or affixed within and/or to the structural frame 418 by one or more mounting screws or set screws 424. Similarly, the optical source 410 and the optical detector 412 may be mounted or affixed within and/or to the structural frame 418 by one or more mounting or set screws 426. The set screws 424, 426 are configured to position and hold the optical elements (e.g., IRE 408, optical source 410, optical detector 412) at required angles relative to each other within the structural frame 418.

In some embodiments, the set screws 424, 426 may be soft-tipped screws that can help with vibration isolation of the components supported (e.g., the IRE 408, the optical source 410, the optical detector 412). The soft-tipped set screws may be tipped with a polymer, plastic, or rubber materials, and may be nylon or the like. If the screws are not fully made from soft or pliable materials, and only tipped with such material, the screws may be made from metal or the like, including, but not limited to steel, stainless steel, brass, etc. The vibration isolation of the components (e.g., the IRE 408, the optical source 410, the optical detector 412) may further be aided by the material that forms the structural frame 418. For example, and without limitation, the structural frame 418 may be made from plastics, thermoplastics, polyethylene, high density polyethylene, polymers, and similar materials. Further, the material of the screws (or tips thereof) may be selected to avoid confounding of data collection (e.g., selected to avoid optical interference).

It will be appreciated that the electronic components (e.g., the optical source 410, the optical detector 412, and electronic components 422) may generate heat. To aid in heat dissipation, the main body 402 may have an open cavity 428 to provide air cooling to the components and remove heat therefrom. One or more vents (not shown) may be arranged about the exterior of the main body 402, to allow airflow through the interior open cavity 428. Further, in some embodiments, a fan or other blower may be arranged within the main body 402 to cause airflow within the open cavity 428. In some such embodiments, vents or the like may be included.

Furthermore, as noted above, the transdermal optical sensing systems of the present disclosure may include mechanisms for detecting the presence of a patient or user of the system. In some embodiments, as described above, such sensors may be arranged on the exterior of the main body. However, as shown in FIG. 4B, one or more detection sensors 430 may be arranged on the structural frame 418. In this configuration, the detection sensors 430 may be pressure sensors, for example. As such, when a user or patient places their wrist on the transdermal optical sensing system 400, the pressure and force of their wrist will be imparted to the structural frame 418, through at least contact with the IRE surface 416. As such, the detection sensors 430 may be configured to detect the presence of a user or patient when performing a measurement. The transdermal optical sensing systems may include other sensors, such as an accelerometer 432, shown in FIG. 4B. The accelerometer 432 may be used for detecting when a patient has placed their wrist in contact with the transdermal optical sensing system. The accelerometer 432 may also be used to monitor vibrations and motions of the transdermal optical sensing system 400. For example, the accelerometer 432 may be configured to monitor for falls or drops of the transdermal optical sensing system 400. If the transdermal optical sensing system 400 falls or is dropped, such impact may cause a change in the calibration and settings, and thus may indicate that the results of a testing or measurement may be incorrect. As such, the accelerometer 432 may be used to detect and/or indicate when recalibration and/or resetting of the system may be required. In a non-limiting example, the calibration curve generated by the system 400 can be analyzed, for example, by comparing the calibration curve generated by the transdermal optical sensing system to a master calibration curve, where the differences between the device calibration curve and the master calibration curve can be indicative of a condition state of the optical sensing system. In an illustrative example, an unadjusted calibration curve of a transdermal optical sensing system may be compared with the master calibration curve for that system, where variances between the curves can be characteristic of certain condition states. In an illustrative example, condition states which may be detected by analysis of the calibration curve can include a damaged condition, a malfunctioning conditioning, a misaligned condition, or a wear condition of the secondary optical device.

Figure 5:
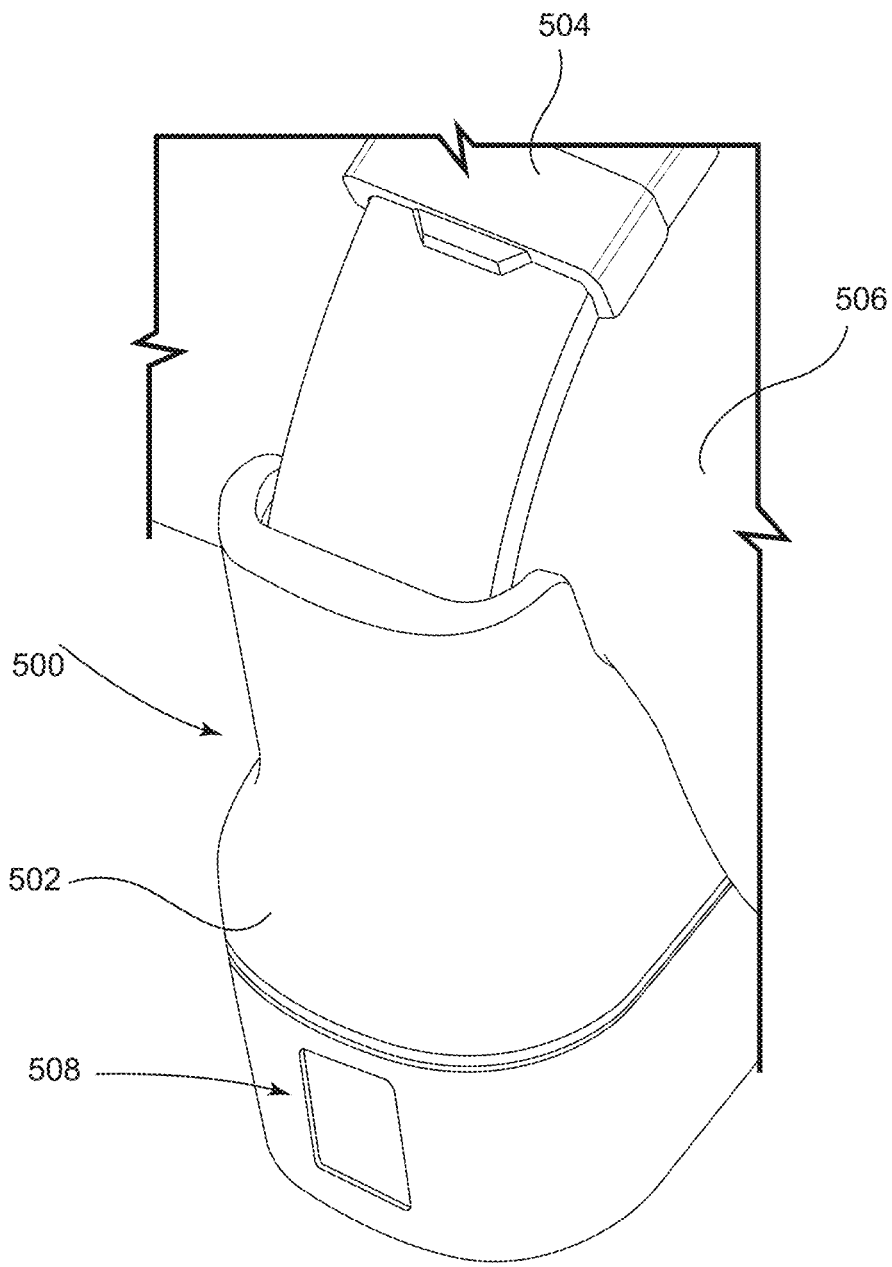
FIG. 5 is a schematic illustration of a transdermal optical sensing system in accordance with the present disclosure, when in use.

Turning now to FIG. 5, a schematic illustration of a transdermal optical sensing system 500 in use and in accordance with an embodiment of the present disclosure is shown. The structural configuration of the transdermal optical sensing system 500 may be substantially similar to that shown and described above. The transdermal optical sensing system 500 includes a main body 502 and a retention member 504. As shown, a patient 506 has their wrist secured to the transdermal optical sensing system 500 by the retention member 504. The retention member 504 provides support to hold the patient 506 in contact with an IRE of the transdermal optical sensing system 500.

In this configuration, the transdermal optical sensing system 500 includes a display 508 on a portion of the main body 502. The display 508 may be controlled by a controller or other electronic component of the transdermal optical sensing system 500. The display 508 may be used to output pertinent information for diagnostic purposes, such as detected levels of a biomarker, chemical, or compound of interest. It will be appreciated that the displayed information may be provided overtime, and thus enables trending of biomarkers in a patient. The display 508 may be used to provide instantaneous or real-time biomarker data/information and may be configured to display such measurements on a continuous basis. The display 508 may thus provide trending information in addition to, or alternative to, a current biomarker measurement. In some embodiments, the display may be separated from the transdermal optical sensing system, and may be part of a personal mobile device, computer, or the like.

Figure 6:
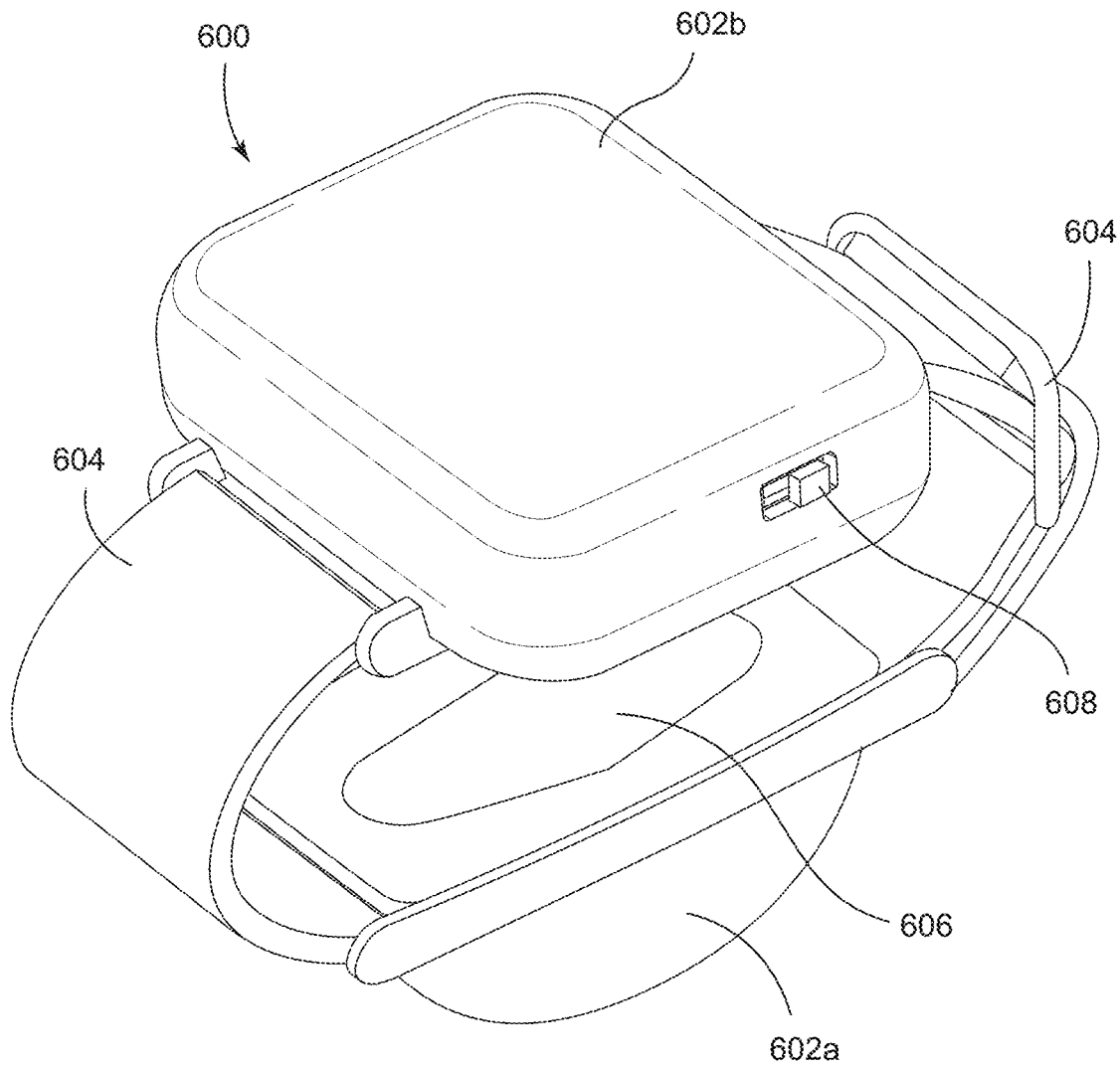
FIG. 6 is a schematic illustration of a transdermal optical sensing system in accordance with an embodiment of the present disclosure.

Although the above described and illustrated embodiments are fairly portable and mobile, in accordance with some embodiments of the disclosure, a more personal version of a transdermal optical sensing system may be provided. For example, with reference to FIG. 6, a schematic illustration of a transdermal optical sensing system 600 in accordance with an embodiment of the present disclosure is shown. The transdermal optical sensing system 600 operates substantially similar to that described above.

The transdermal optical sensing system 600, in this configuration, includes two main body portions 602a, 602b that are configured to house power and control features of the transdermal optical sensing system 600 (e.g., controller, electrical power, etc.). A first main body portion 602a may house the optical components and a second main body portion 602b may house the processing and control components of the transdermal optical sensing system 600. In this configuration, the transdermal optical sensing system 600 is arranged as a watch-type device or wrist-wearable and may be worn by a patient. As such, the transdermal optical sensing system 600 includes two retention members 604 that form a wristband or similar structure. The transdermal optical sensing system 600 includes an IRE 606 on the first main body portion 602a for contact with the skin of a patient that wears the transdermal optical sensing system 600. An operational button 608 may be provided to perform measurements on demand and/or for powering the transdermal optical sensing system 600 on and off.

Figure 7:
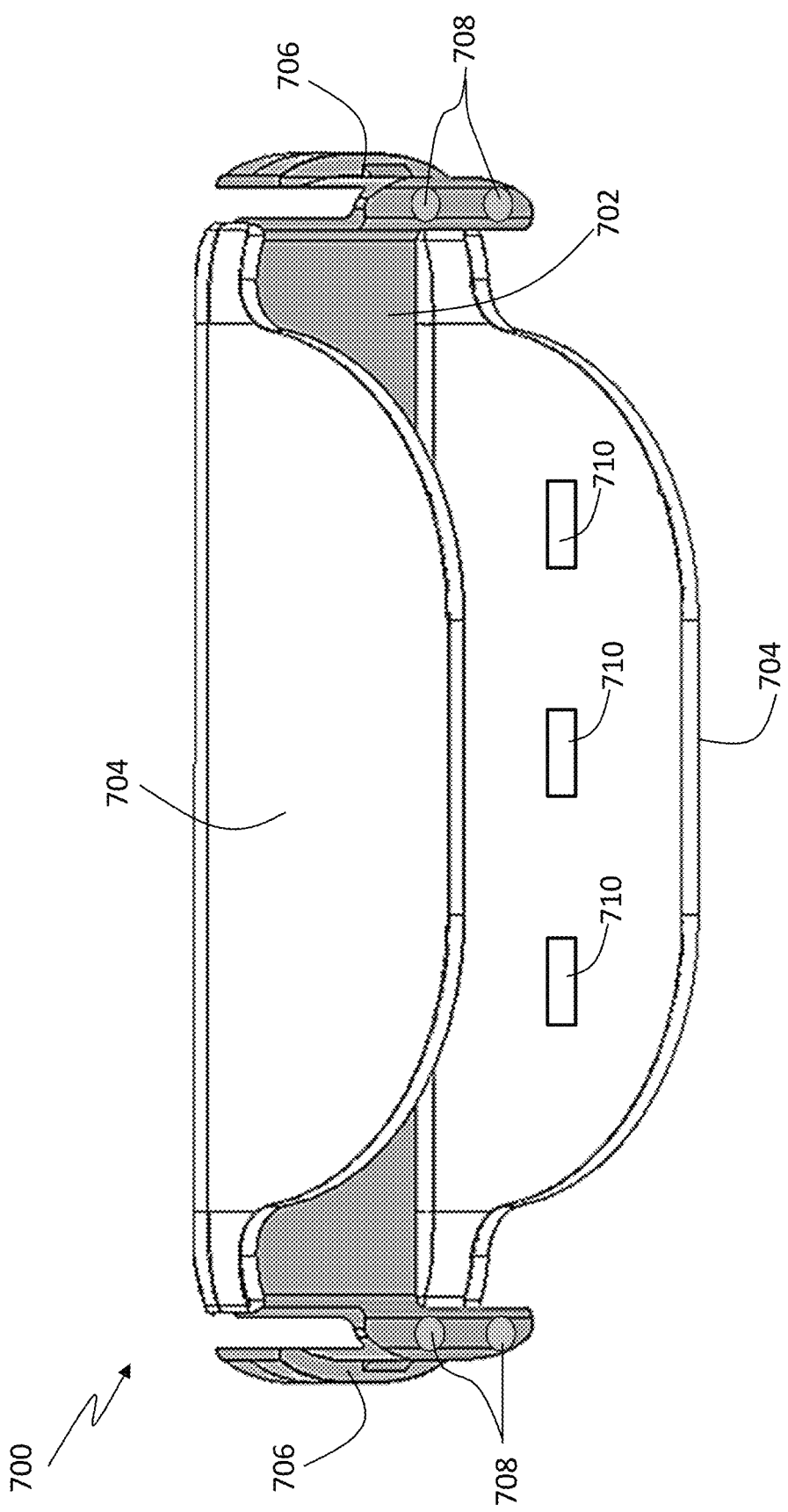
FIG. 7 is a schematic illustration of a cover of a transdermal optical sensing system in accordance with an embodiment of the present disclosure.

Turning now to FIG. 7, a schematic illustration of a cover 700 of a transdermal optical sensing system in accordance with an embodiment of the present disclosure is shown. The cover 700 may be used with any of the above described transdermal optical sensing systems or variations thereon. The cover 700 is shown structurally to fit on the above described transdermal optical sensing systems, but such geometry and shape is not to be limiting and the cover may take other shapes, depending, for example, upon the geometry of the main body of the transdermal optical sensing system.

The cover 700 includes a top wall 702 and two sidewalls 704. As shown, the cover 700 includes clips 706 configured to snap-engage with a main body of a respective transdermal optical sensing system. It will be appreciated that other types of connections between the cover 700 and the main body may be employed without departing from the scope of the present disclosure. For example, in some non-limiting examples, a magnetic connection, the use of hooks, or the like may be used.

The cover 700, in this embodiment, includes electrical contacts 708 for transmission of electrical power from the main body into the cover 700. The cover 700 further includes one or more UV light emitters 710. The UV light emitters 710 may be powered through electrical power provided through the electrical contacts 708. The UV light emitters 710 may be arranged and angled such that light generated at the UV light emitters 710 are directed at an IRE of the transdermal optical sensing system to which the cover 700 may be attached. Such configuration enables disinfecting of the IRE through application of UV light incident thereto. Although shown with the UV light emitters 710 arranged on one sidewall 704 of the cover 700, it will be appreciated that such UV light emitters 710 may be included on both sidewalls 704 of the cover 700. Further, any number of UV light emitters 710 may be employed. Moreover, although described as UV light emitters, the cover 700 can include one or more types of emitters to generate light that may be used to disinfect or otherwise sanitize the IRE and other surfaces of the transdermal optical sensing system.

Figure 8:
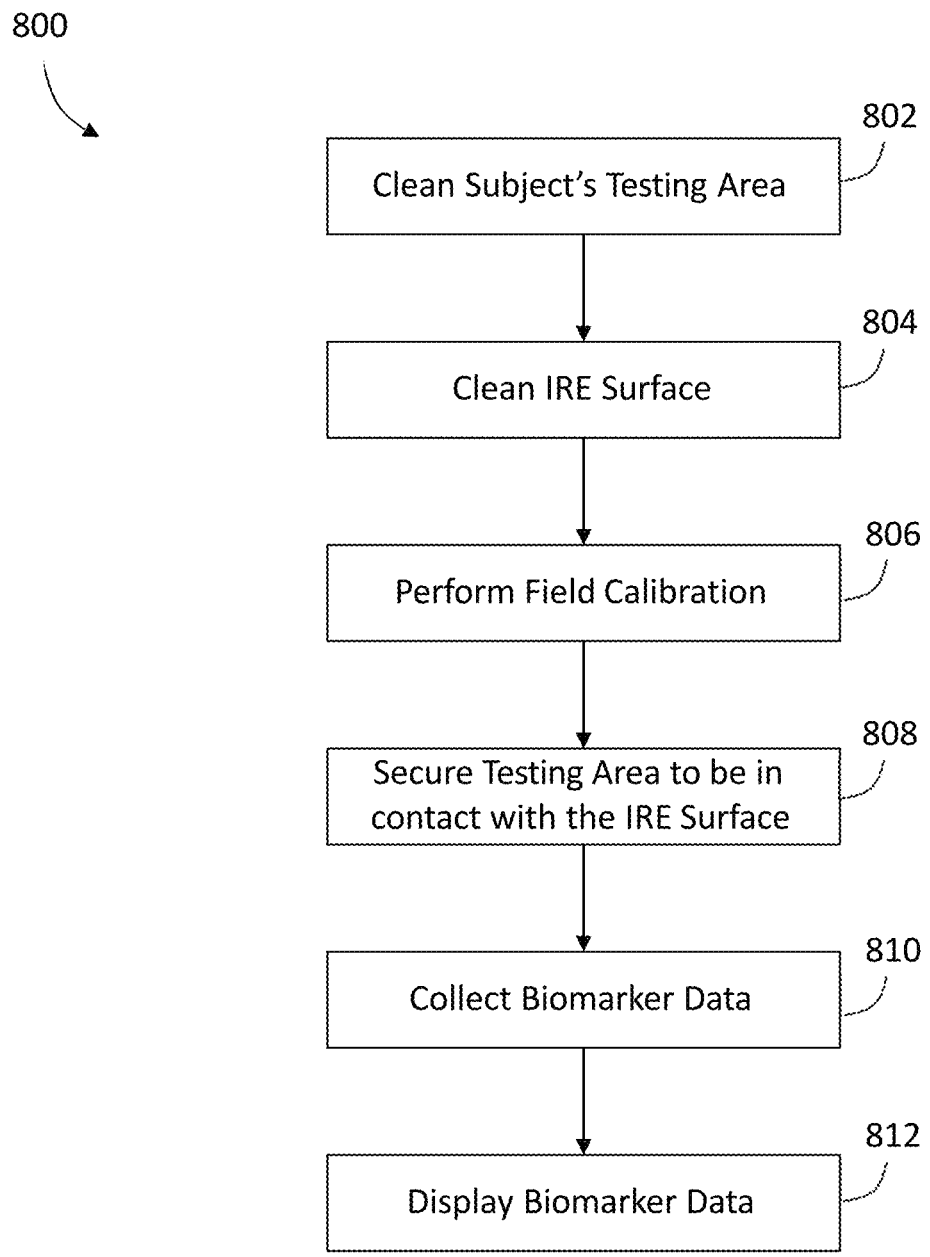
FIG. 8 is a flow process for using a transdermal optical sensing system in accordance with an embodiment of the present disclosure.

Turning now to FIG. 8, a flow process 800 for using a transdermal optical sensing system in accordance with an embodiment of the present disclosure is shown. The flow process 800 may be employed with one or more of the above described transdermal optical sensing systems or variations thereof.

At step 802, a patient's or subject's testing area is cleaned. For example, the inside area of the wrist is cleaned. The cleaning may be by saline and/or alcohol solutions, or the like. It will be appreciated that the cleaning step may include additional preparation steps, such as inspecting the area on the patient, etc. Further, although referred to here with respect to the wrist, it will be appreciated that other parts of the body may be employed for purposes of the flow process 800, and the current description is not intended to be limiting to only wrist applications.

At step 804, an IRE is cleaned. The cleaning of the crystal surface may be cleaned, for example, with latex-free gauze dampened with saline solution followed by 91% rubbing alcohol. Latex-free gauze may then be used to wipe dry the surface. In some embodiments, step 804 may include disinfecting and/or sterilizing, which encompasses more than just cleaning. In some such embodiments, the transdermal optical sensing system may include an integrated cleaning system. For example, a cover of the transdermal optical sensing system may include one or more UV light sources that can be used to disinfect the IRE surface and/or other surfaces of the transdermal optical sensing system that may come into contact with a subject (e.g., patient's wrist).

Steps 802, 804 are preparation steps to ensure that measurements are no contaminated with debris, materials, oils, or the like, on human skin and/or the IRE surface.

At step 806, the transdermal optical sensing system may be operated to perform a field calibration. The field calibration step 806 may be used as a baseline to filter out background detections. For example, the field calibration step 806 may be used to create a data set to filter out ambient light, external influences, and/or impacts on the measurements taken using the transdermal optical sensing system. The field calibration may be used for detection of motion artifacts, noise correction, assessing sensor falls/drops, etc. As these things may impact the measurements taken of the subject, this information and calibration can be used to ensure proper measurements are taken or at least corrected for to remove noise or the like in the data sets. The field calibration may include noise correction, checking of accelerometer data, etc. to calibrate the system for a specific data collection.

At step 808, the subject's cleaned testing area is secured to transdermal optical sensing system such that the testing area is in contact with the cleaned IRE surface. For example, a wristband or other retention member is used to secure and/or fasten the subject's wrist to be in contact and centered with respect to the IRE. Tension of the retention member may be adjusted so that the retention member does not restrict blood flow or cause discomfort to the subject.

At step 810, the transdermal optical sensing system is operated to collect biomarker data. The biomarker data may include one or more biomarker measurements of Troponin I, Troponin T, CKMB, BNP, NTproBNP, FABP3, Myoglobins, and/or other biomarkers. In some embodiments, the data may be collected for a predetermined amount of time. For example, in one no-limiting embodiment, the transdermal optical sensing system may be operated for about 5 minutes to collect data throughout the time period. It will be appreciated that other time periods may be used, such as 1 minute, 2 minutes, 10 minutes, 15 minutes, etc. Further, in some instances, the transdermal optical sensing system may be worn for prolonged periods of time, such as hours, or even days. During such time, the transdermal optical sensing system may collect data continuously, at predetermined intervals, or upon demand (e.g., manual activation to collect biomarker data) by a doctor or other user, for example. During the biomarker data collect of step 810, time stamps may be collected and associated with the data collection, and thus time-based trending of biomarker levels may be achieved.

During step 810, the transdermal optical sensing system may be operated to generate light at one or more specific or predefined wavelengths. The generated light may be from an optical source within the transdermal optical sensing system. The light is directed into the IRE, where the light will interact with the IRE surface and the testing area of the subject. The light will be internally reflected within the IRE, and an optical detector or sensor is arranged to detect the light that interacts with the testing area. The detected light may be analyzed for peaks at one or more wavelengths to detect the presence of the biomarkers.

At step 812, the collected biomarker data is displayed. The display of the biomarker data may be on a screen or display of the transdermal optical sensing system and/or on a remote display. In some configurations, the display of the data may be on a remote personal device, such as a mobile phone, tablet, computer, or the like. In some instances, the transdermal optical sensing system may be configured to transmit the collected biomarker data directly to a connected device (e.g., by Bluetooth connection) or through a network (e.g., internet and/or cloud data system) which is then transmitted to a device for display, such as a computer or other device. In some instances, the transmission of the collected biomarker data may be through a wired connection, such as a USB connection from the transdermal optical sensing system to another device.

With the displayed biomarker data, a health professional may be able to make determinations regarding a patient's health with respect to the biomarkers detected. As such, appropriate care procedures may be implemented. Advantageously, the transdermal optical sensing systems of the present disclosure provide for real-time data collection and display and/or for data trending based on real-time, in situ measurements. In some embodiments, a blood draw may be required from the subject to confirm or further check for one or more biomarkers. It will be appreciated that the transdermal optical sensing systems of the present disclosure may be used to perform real-time, continuous monitoring of biomarkers in a non-invasive manner.

It will be appreciated that one or more of the steps of flow process 800 may be omitted or performed in a different order, without changing the scope of the process. For example, one or more of the cleaning steps 802, 804 and/or the ambient measurement of step 806 may be performed in a different order or may be omitted entirely.

The transdermal optical sensing systems of the present disclosure provide for an optical detector that is portable (e.g., palm-sized) and employs a broadband infrared light source, a germanium IRE, and a thermopile detector with filters sensitive to multiple optical ranges. In some embodiments, the thermopile detector (e.g., optical detector described above) may be configured with two different filters. In one such non-limiting embodiment, the first filter is representative of an Amide II band which is used as an internal standardizing reference and the second filter has an optical range (e.g., by frequency) chosen such that cTnI would have the largest contribution to the absorption as a function of the cTnI concentration. Due to the absence of moving parts and complex optical components, the small form factor is achieved in accordance with embodiments of the present disclosure while minimally affected by mechanical vibrations.

In accordance with some non-limiting embodiments, the filters may include a base semiconductor such as silicon, Gallium Nitride, Germanium or Indium Phosphide. Micro layers of organic or inorganic semiconductors are deposited on the base material, or it is doped with metals, to obtain a dielectric coating, the thickness of which tunes the transmission/absorption of certain wavelengths of light. The deposition methods can be Chemical Vapor Deposition, Molecular Beam Epitaxy, Metal Oxide Chemical Vapor Deposition, or energetic sputtering.

In accordance with some embodiments of the present disclosure, the effect of stray light impacting diagnostic analysis may be negated by pulsing the optical source (e.g., an optical emitter) at 4 Hz while polling the thermopile (e.g., optical detector or sensor) at 8 Hz. In accordance with embodiments of the present disclosure, the pulsing of the detector may be set at an integer multiple of the pulsing of the optical source or emitter. For example, the detector may have a pulsing rate that is double, triple, quadruple, etc. the pulsing rate of the emitter. The pulsing rate of the emitter may be selected as desired and may be a rate of 2 Hz or greater, for example. This results in recording both the on and off state of the emitter. A differential of these two states will account for the extraneous light captured by the detector. In accordance with some embodiments, based on the fourth universal definition of myocardial infarction, as informed by the $99^{th}$ percentile of troponin-I distribution in a reference population, a decision threshold of 19 ng/L is established for Myocardial Infarction diagnosis. It will be appreciated that other pulsing rates, polling rates, and decision thresholds may be employed without departing from the scope of the present disclosure.

When using Attenuated Total Reflectance (ATR) to interrogate the presence of cardiac biomarkers using infrared light, the returning evanescent light from the skin back into the IRE surface contains information that is indicative of the presence or absence of cardiac biomarkers. The penetration depth of the optical light generated by the optical sources is sufficient to interact with interstitial fluid within a patient's body. For human skin, the approximate penetration depth is about 1-10 micrometer indicating that the light could potentially interact with the epidermis and the interstitial fluid with the IRE surface placed under the wrist of a patient (palmar surface). In some embodiments, the directed light may interrogate sweat glands and/or other superficial glands through the epidermis of a patient. As such, the incident light may interrogate subsurface features of a patient and thus enable detection of specific chemicals and/or compositions that may be indicative of a patient's health.

Owing to the modality of optical data collection, in some embodiments, the IRE and/or optical detector may be susceptible to light pollution and ambient conditions. This may be mitigated by pulsing the optical source such that the detector is configured to differentially measure during both on and off states. Furthermore, in some embodiments, a blank background measurement may be conducted prior to installation on the patient. Such background measurement may be used to eliminate dependencies on ambient conditions.

In some embodiments, the optical source and the optical receiver may be configured with four optical bands to obtain a differential measurement. This enables a higher correlation to troponin by minimizing the contribution to optical absorption from other optical confounders in the measurand. Noise handling algorithms and outlier detection techniques may be implemented to improve accuracy of detection. Such techniques may be implemented by leveraging deep learning and/or neural networks, for example.

According to some embodiments of the present disclosure, a risk stratification system and method includes a non-invasive biomarker sensor, a controller, and an analyzer to detect a physiological state of the subject being monitored, such as myocardial injury or stress. In accordance with some embodiments, a wearable device includes a non-invasive biomarker sensor and a controller for sending optical signals from the non-invasive biomarker sensor to an analyzer within the device or over wireless communication to a cloud-based end point (e.g., through an internet or other wireless or wired connection). The wearable devices, in some embodiments, includes an infrared source, an optical component such as an internal reflecting element (IRE), and an IR detector with specific broad and narrow-band filters. Other optical components such as light pipes, waveguides, parabolic or flat mirrors, linear or circular polarizers may also be used to optimize the efficiency of light detection. Such additional optical components, for example, may be housed within the main body of the transdermal optical sensing systems described herein. The optical sources, also referred to herein as emitters, of various embodiments can include, without limitation, lasers, light emitting diodes (LEDs), radiative thermal light sources, or other such sources. The optical sources may be configured to generate and output infrared light.

For detecting one or a combination of many biomarkers representing myocardial injury or stress, optical filters that allow the passage of specific wavelengths of infrared light that are employed. The optical filters may be incorporated into the optical receivers of the transdermal optical sensing systems described above. The optical filters can be configured to allow for specific interrogation of biomarkers, or a combination thereof. For example, two absorbance wavelength ranges, 6.4-6.9 micrometers and 8-14 micrometers may be used to detect levels of biomarkers such as, but not limited to, Troponin I, Troponin T, CKMB, BNP, NTproBNP, FABP3, Myoglobins, etc. The optical filters can allow infrared light in these two absorption bands to pass through. The optical filters can be used anywhere along the light path. In one non-limiting embodiment, the filters may be directly mounted on the optical detector.

Optical detectors in accordance with embodiments of the present disclosure, and without limitation, can include thermal (pyroelectric, bolometers, microbolometers, etc.) or photonic (thermocouples, thermopiles, etc.) types. Customized optical detectors (e.g., quantum structure based) that are inherently sensitive to specific wavelength windows as mentioned above can be used in lieu of, or in combination with, the optical filters described above to perform diagnostic analysis. Further, single or multiple pass IRE may be used to allow the optical interaction of the light with that of the exposed skin that comes in contact with the IRE surface. The IRE can be made of materials including, but not limited to Germanium, Silicon, Diamond, Indium Phosphide, Sapphire, Zinc Sulphide, Zinc Selenide, Quartz, etc. The optical sensor device, which is an integration of the aforementioned components, can be mounted on or placed in contact with any part of the human body such that the IRE is directly in contact with exposed skin. In one such embodiment, the optical sensor device is fashioned as a wrist wearable where the IRE surface comes in contact with the underside of the wrist while the device is held in place by means of a strap or other retention member.

In operation of transdermal optical sensing systems described herein, the controller includes a computer-implemented method. The method is performed to characterize the differential measurement of optical intensities of light sent from the optical source and received at the optical detector, before and after it passes through the material. In some embodiments, a calibration step is performed with reference to a background data measurement (e.g., ambient conditions without a patient in contact with the IRE surface). In some embodiments, the systems and methods may include a distributed biomarker trend analysis. Such trend analysis may include, without limitation, real-time myocardium analysis based on the trend in cardiac biomarkers, in reference to baseline levels of a patient. Further, real-time myocardium analysis may be performed based on a trend in specific cardiac biomarkers, in reference to demographics 99th percentile upper reference limit. Further still, personalized triage and alert workflows for healthcare providers, patients, and caregivers may be achieved. The transdermal optical sensing systems described herein enable continuous recording and reporting of biomarker information over time. As such, biomarker baselines and trending may be achieved for individual patients. The real-time data collection and display enables improved medical diagnostics due to the ability to detect fluctuations and/or variations from a baseline or the like, for example.

According to some embodiments, the transdermal optical sensing systems can enable a risk classification of high risk, intermediate risk, and low risk of patients. Effective early risk stratification in outpatient health care facilities can help reduce the burden of chest pain evaluation in Emergency Departments and can guide high-risk patients toward more prompt care including coronary angiography and potentially earlier revascularization. For intermediate to low risk patients, continuous inpatient monitoring can also help distinguish the individuals who would benefit from an earlier invasive versus non-invasive approach, thus expediting care and discharge from the hospital. Once established as low risk, patients can proactively be monitored for recurring cardiac complications.

Advantageously, embodiments described herein provide for non-invasive devices for monitoring patient wellbeing. In accordance with some embodiments, a patient-centric modality for troponin-I monitoring is provided that can inform efficient triaging and timely intervention in a cardiac clinical workflow. The devices and processes disclosed herein enable remote monitoring capability to empower cardiologists in determining a timely clinical course of action to prevent unnecessary myocardial injury.

Also disclosed and described are wearable sensors that may be worn in a watch-style configuration and may be used in combination with a worn heart rate monitor, such as an EKG vest, or other medical monitoring system. That is, embodiments of the present disclosure may be employed in combination with other health sensors to develop and monitor the health of a patient. It will be appreciated that such heart rate monitors or other monitoring devices and systems may be employed with any of the transdermal optical sensing systems described herein, and such combination of devices is not limited to the watch-type systems. Such use of multiple devices for multiple different patient variables (e.g., biomarker levels, heart rate, blood pressure, etc.) may enable further improved patient health care outcomes and responses.

Figure 9:
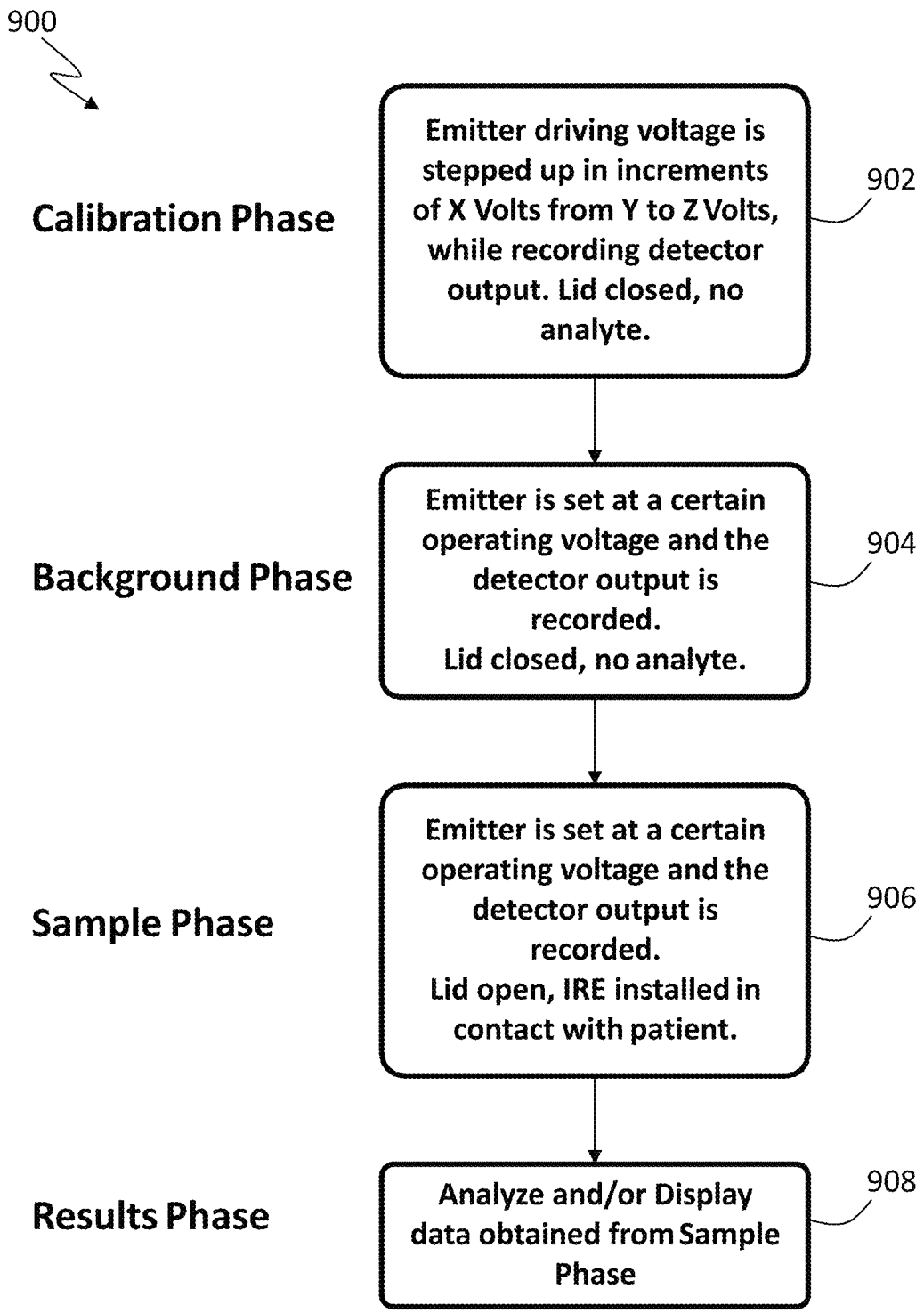
FIG. 9 is a flow process for using a transdermal optical sensing system in accordance with an embodiment of the present disclosure.

Turning now to FIG. 9, a flow process 900 for using a transdermal optical sensing system in accordance with an embodiment of the present disclosure is shown. The flow process 900 may be performed automatically using any of the above described transdermal optical sensing systems and/or variations thereon. The process 900 is broken separated into different phases: calibration phase 902, background (ambient) phase 904, sample phase 906, and results phase 908. The process 900 may be initiated by pressing a button or toggle on the transdermal optical sensing system or otherwise initiating the process (e.g., from a mobile device, connected computer, or the like).

During the calibration phase 902, a voltage is applied to an emitter of the transdermal optical sensing system to perform the initial calibration. The applied voltage is applied in a stepped fashion in voltage increments (e.g., of X volts) from a first or initial voltage (e.g., Y volts) to a second or final voltage (e.g., Z volts). In some configurations, the initial voltage is less than the final voltage (e.g., increasing increments). In other configurations, the initial voltage is greater than the final voltage (e.g., decreasing increments). During the stepped voltage application (e.g., emitted driving voltage), a detector is operated to detect output from the emitter, and such detections may be recorded, for example, as a dataset including each applied voltage paired with the detector output corresponding to the applied voltage. Such data recordation may be local onboard the transdermal optical sensing system or may be transmitted to a remote device (e.g., computer, mobile device, remote server, cloud, etc.). During this process, the lid or cover of the transdermal optical sensing system is in place and there is no analyte present. That is, the calibration phase 902 is performed in isolation from the external environment and without a patient in contact therewith.

During the calibration phase, and in one non-limiting example, the emitter may be pulsed at 4 Hz between a high state and a low state and the detector may be polled at 8 Hz. The high state may be a maximum output from the emitter during the cycling of the pulses. The low state may be a minimum output from the emitter during the cycling of the pulses. In some embodiments, the low state may be an off state or a state in which nothing is emitted from the emitter. However, in other embodiments, the low state may be low power emission from the emitter, and thus the low state is not required to a fully off or zero level. In one non-limiting example, the voltage step during the calibration phase 902 may be between 1 volt and 4 volts with increments of 0.2 volts.

During the calibration phase 902, the recorded data at the detector is used to establish a baseline for the specific transdermal optical sensing system. This baseline may be aligned with a master dataset that is established to conform the data obtained using the transdermal optical sensing system with known data output such that when the transdermal optical sensing system is used with a patient (sample phase 906), the output from the transdermal optical sensing system may be accurate and consistent. The master dataset can also be referred to herein as a baseline dataset. During the calibration phase 902, an analysis algorithm of or associated with the transdermal optical sensing system may be adjusted based on the stepped voltage process to align the readings of the detector with a known (e.g., master device) transdermal optical sensing system.

During the background phase 904, the transdermal optical sensing system is operated again (with lid closed, no analyte) at a specific known operating voltage. The voltage of the background phase 904 will be a voltage within the voltage range between the initial voltage and the final voltage of the calibration phase 902. This step enables detection of ambient and/or environmental influence upon the data readings of the transdermal optical sensing system. This information may be stored in an onboard or remote memory that is within or associated with the transdermal optical sensing system. The background phase 904 can also be referred to herein as the ambient phase.

During the sample phase 906, a patient is placed in contact with the transdermal optical sensing system (e.g., wrist of the patient) and the transdermal optical sensing system is operated. During the sample phase 906, the emitter is set at the same operating voltage as used in the background phase 904. In this phase, the lid is open and the optical components of the transdermal optical sensing system (e.g., internal reflection element). The emitter is pulsed and optical data is collected using the transdermal optical sensing system.

In both the background phase 904 and the sample phase 906, the emitter may be operated at the same pulse cycle as used in the calibration phase.

During the results phase 908, the data obtained is analyzed to determine features of interest (e.g., biomarker levels) related to the patient. The analysis during the results phase 908 may include adjusting or transforming the data collected based on the calibration phase 902 and/or the background phase 904. For example, the data collected may be adjusted to remove background noise information that is obtained during the background phase 904. Further, the data obtained may be adjusted based on a mathematical transformation to adjust the collected data to align with the known values associated between data collection and biomarker levels from the master device or master transdermal optical sensing system. With these adjustments, the used transdermal optical sensing system may be configured to display biomarker levels (e.g., display values) or such date/information of biomarker levels may be transmitted for use by a medical professional or the like.

Figure 10:
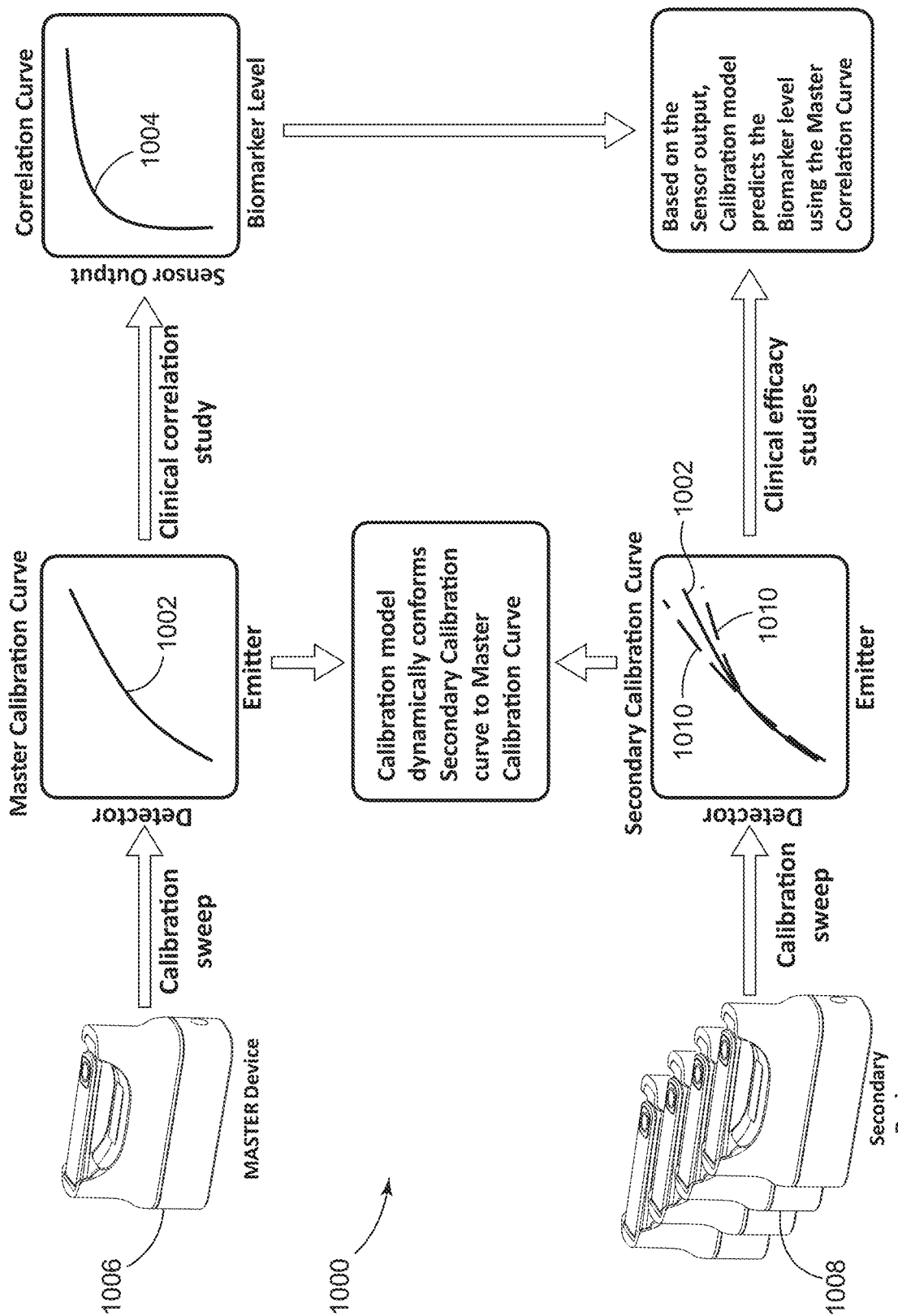
FIG. 10 is a schematic diagram for calibrating transdermal optical sensing systems in accordance with an embodiment of the present disclosure.

Turning now to FIG. 10, a flow process 1000 for calibration and use of transdermal optical sensing systems in accordance with the present disclosure is shown. The flow process 1000 starts by establishing a master calibration curve 1002 and a correlation curve 1004 based on a master device 1006 (e.g., a transdermal optical sensing system as shown and described above). The master device 1006 is operated to perform a calibration sweep, similar to the calibration phase 902 of flow process 900 in FIG. 9. For example, the master device 1006 is operated to perform a stepped voltage operation where the emitter of the master device 1006 is operated in a cyclical manner. From this, the master calibration curve 1002 is established.

The master calibration curve 1002 is a representation of the electrical and optical components of the master device 1006. Under perfect conditions, the output from the emitter and the input received at the detector would have a linear relationship (1:1) such that as the voltage is increased, the output levels from the emitter and the input levels at the detector should be equal or at least linearly correlated. However, due to imperfects, manufacturing tolerances, etc., a non-linear relationship will typically be observed. This relationship between the output of the emitter and the is represented by the master calibration curve 1002.

The master device 1006 is then used within a clinical correlation study to correlate sensor outputs with biomarker levels of interest. This may be based on obtaining outputs from the master device 1006 and comparing and correlating this output with lab values such that the output is assigned to a known lab value. From this, the correlation curve 1004 is determined. That is, based on the master device 1006, output from a sensor is correlated or assigned biomarker level values.

Next, one or more secondary devices 1008 (e.g., transdermal optical sensing systems) are manufactured and must be calibrated to ensure that when the secondary sensors 1008 are used, the output from such secondary sensors 1008 may have a high level of confidence. As such, a factory calibration may be performed with each secondary device 1008 to calibrate the secondary device 1008 to the master device 1006. During this process, the secondary device 1008 is operated to perform a calibration phase (e.g., calibration phase 902 of process 900). During this calibration phase, each voltage paired with the corresponding output is recorded to a secondary dataset; and a secondary calibration curve 1010 is obtained for each secondary device 1008, where the secondary calibration curve 1010, as initially obtained from the secondary device 1008, can be referred to herein as an unadjusted calibration curve. As illustrative shown in FIG. 10, the secondary calibration curves 1010 may be different from the master calibration curve 1002. Although the secondary devices 1008 are substantially similar to the master device 1006, the specific physical components (e.g., IRE, detector, emitter, electronics, etc.) may all impart small changes to the optical readings of each individual device 1006, 1008.

To ensure proper biomarker detection and readings using each secondary device 1008, the unadjusted secondary calibration curve 1010 will need to be adjusted such that it aligns with the primary calibration curve 1002. To make this adjustment a calibration model may be employed. In some non-limiting embodiments, the calibration model may be a machine learning ("ML") model. In such embodiments, the ML model can be any machine learning model, such as a binary classification, a multiclass classification, a regression model, etc., as will be appreciated by those of skill in the art. In accordance with some such embodiments, the ML model may be trained as a supervised or an unsupervised model. In other embodiments, the calibration model may not be based on machine learning but may be otherwise implemented. For example, the calibration model may be a fixed or manually adjusted model that is established based on other parameters as known in the art. The calibration model is a mathematical model that performs an operation upon the secondary calibration curve 1010 to adjust the curve to align with and/or match the master calibration curve 1002. Such calibration model may perform a linear adjustment (e.g., merely adjust values of the secondary sensor by a fixed amount), quadratic adjustment, polynomial adjustment, matrix adjustment, or other mathematical adjustment to ensure that the secondary calibration curve 1010 is adjusted or transformed to align with the master calibration curve 1002. That is, the calibration model is used to dynamically conform the secondary calibration curve to the master calibration curve.

Subsequently, the secondary devices 1008 may be used to perform clinical studies or obtain clinical data. Because the secondary devices 1008 have been calibrated to the master calibration curve 1002, when the secondary devices 1008 are used, the outputs therefrom may be interpreted based on the correlation curve 1004 that was established using the master device 1006. That is, based on the output from the secondary device 1008 and the transformation or adjustment determined from the calibration model, the biomarker levels of a patient may be accurately determined.

In some embodiments, every time a given device is activated to perform a sensing detection with a patient, the calibration of FIGS. 9-10 may be performed. As such, with a given secondary device 1008, the calibration model (or implementation thereof) may change because the secondary calibration curve 1010 may change each time the secondary device 1008 is used. That is, the adjustment made to the secondary calibration curve 1010 for a given secondary device 1008 may change from one use to another use. As such, the calibration with the master device 1006 described herein may be performed automatically every time the secondary device 1008 is used. For example, the calibration phase 902 of process 900 may include a step of obtaining a secondary calibration curve, running the calibration model to adjust or conform the secondary calibration curve to a master calibration curve, and then continuing with the procedure.

In some embodiments, the calibration model may be a model stored onboard memory of the given transdermal optical sensing system, and thus the calibration may be performed all within a given device. In other embodiments, the secondary calibration curve may be transmitted to a remote system (e.g., mobile device, computer, cloud, etc.) to be conformed to the master calibration curve, and the resulting adjustment operation may be transmitted back to the transdermal optical sensing system to be used during operation. Further still, in other embodiments, rather than receiving the calibration adjustment at the device, the transdermal optical sensing system may proceed to the background and samples phases (e.g., as described with respect to FIG. 9), and the results phase may include transmitted such results to the remote location, where the data is adjusted based on the calibration model.

The following Clauses provide example configurations of a method and system for calibrating an optical sensing system, and a method for operating a transdermal optical sensing system, as disclosed herein.

Clause 1. A method of calibrating an optical sensing device, wherein the optical sensing device includes an emitter, a detector, and an optical component coupled to the emitter and the detector, the optical sensing device further including a power source and electronics including a controller, the method comprising: isolating the optical component from an external environment; applying a plurality of voltages to the emitter; detecting, via the detector, an output corresponding to each voltage; recording each voltage paired with the corresponding output to a baseline dataset; wherein the plurality of voltages includes an initial voltage, a final voltage, and incremental voltages stepped by a voltage increment between the initial voltage and the final voltage; and generating, using the baseline dataset, a calibration curve.

Clause 2. The method of clause 1, wherein the initial voltage is less than the final voltage.

Clause 3. The method of clause 1, wherein the initial voltage is greater than the final voltage.

Clause 4: The method of clause 1, wherein the voltage increment is an increase in voltage.

Clause 5. The method of clause 1, wherein the voltage increment is a decrease in voltage.

Clause 6. The method of clause 1, wherein the voltage is stepped from an initial voltage of 1 volt to a final voltage of 4 volts.

Clause 7. The method of clause 6, wherein the voltage increment is 0.2 volts.

Clause 8. The method of clause 1, wherein the calibration curve is non-linear.

Clause 9. The method of clause 1, wherein the calibration curve is generated by the controller.

Clause 10. The method of clause 1, wherein applying the plurality of voltages to the emitter includes: pulsing the emitter at a frequency of 4 Hertz (Hz) between a high power emission state and a low power emission state of the emitter; and polling the detector at a frequency of 8 Hertz (Hz).

Clause 11. The method of clause 10, wherein the low power emission state is an off state of the emitter.

Clause 12. The method of clause 10, wherein the low power emission state is a powered state of the emitter.

Clause 13. The method of clause 10, wherein the high state is a maximum output of the emitter.

Clause 14. The method of clause 1, wherein the optical component is an internal reflection element.

Clause 15. The method of clause 1, where the optical component includes at least one of a crystal, a prism, light pipe, a waveguide, a parabolic mirror, a flat mirror, a linear polarizer, or a circular polarizer.

Clause 16. The method of clause 1, wherein the optical sensing device is operable to transmit data to an external component including a processor, the method further comprising: transmitting, via the optical sensing device, the baseline dataset to the external component; wherein the external component is operable to: generate the calibration curve; and transmit the calibration curve to the optical sensing device; the method further comprising: receiving, via the optical sensing device, the calibration curve.

Clause 17. The method of clause 1, wherein the optical sensing device is a master optical sensing device and the calibration curve is a master calibration curve, the method further comprising: providing a secondary optical device including a secondary emitter, a secondary detector, a secondary optical component, a power source and electronics including a secondary controller; calibrating the secondary optical device by: isolating the secondary optical component from the external environment; applying the plurality of voltages to the secondary emitter; detecting, via the secondary detector, an output corresponding to each of the voltages; recording the outputs to a secondary dataset; generating a secondary calibration curve by: generating an unadjusted calibration curve based on the secondary dataset; adjusting, using a calibration model, the unadjusted calibration curve to align with the master calibration curve.

Clause 18. The method of clause 17, wherein the secondary optical device is operable to transmit data to an external component including a processor, the method further comprising: transmitting, via the secondary optical device, the secondary dataset to the external component; wherein the external component is operable to: generate the secondary calibration curve using the secondary dataset; and transmit the secondary calibration curve to the secondary optical device; the method further comprising: receiving, via the secondary optical device, the secondary calibration curve.

Clause 19. The method of clause 17, wherein the calibration model is operable to adjust the unadjusted calibration curve to align with the master calibration curve by performing an adjustment selected from the group consisting of a linear adjustment, a quadratic adjustment, a polynomial adjustment, and a matrix adjustment.

Clause 20. The method of clause 17, wherein the calibration model is a machine learning module selected from the group consisting of a binary classification model, a multiclass classification model, and a regression model.

Clause 21. The method of clause 17, wherein the calibration model is a supervised machine learning module.

Clause 22. The method of clause 17, wherein the calibration model is an unsupervised machine learning module.

Clause 23. The method of clause 17, further comprising: analyzing the unadjusted calibration curve to determine a condition state of the secondary optical device.

Clause 24. The method of clause 23, wherein the condition state corresponds to at least one of a damaged condition, a malfunctioning conditioning, a misaligned condition, or a wear condition of the secondary optical device.

Clause 25. The method of clause 23, wherein analyzing the unadjusted calibration curve includes at least one of: comparing the unadjusted calibration curve to the master calibration curve; and comparing the unadjusted calibration curve to the secondary calibration curve.

Clause 26. The method of clause 1, wherein the optical sensing device is operable as a transdermal optical sensing device for monitoring at least one biomarker in a subject, the method further comprising: generating a biomarker correlation curve for the at least one biomarker; wherein generating the biomarker correlation curve includes: for each subject of a plurality of subjects: recording a detector output from the optical sensing device in contact with the subject; wherein the detector output corresponds to a predetermined operating voltage of the emitter; and obtaining a corresponding laboratory value of the at least one biomarker of the subject; and correlating, using the detector output and the corresponding laboratory value of the at least one biomarker obtained from the plurality of subjects, the detector output to the values of the at least one biomarker; wherein the biomarker correlation curve correlates the detector output to a value of the at least one biomarker.

Clause 27. The method of clause 26, wherein the predetermined operating voltage is a voltage between the initial and final voltage.

Clause 28. The method of clause 26, wherein the at least one biomarker includes a first biomarker and a second biomarker, the method further comprising: generating a first biomarker correlation curve for the first biomarker; and generating a second biomarker correlation curve for the second biomarker.

Clause 29. The method of clause 26, wherein the at least one biomarker includes a combination biomarker defined by a combination of a first biomarker and a second biomarker, the method further comprising: generating a combination correlation curve for the combination biomarker.

Clause 30. The method of clause 26, wherein the at least one biomarker is indicative of a physiological state of the subject.

Clause 31. The method of clause 30, wherein the physiological state of the subject includes a myocardial state.

Clause 32. The method of clause 26, further comprising: positioning the optical sensing device in contact with a subject; activating the emitter at the predetermined operating voltage; recording a detector output from the optical sensing device in contact with the subject; determining, using the detector output and the biomarker correlation curve, a value of the biomarker of the subject.

Clause 33. The method of clause 32, further comprising: isolating the optical sensing device from the external environment; applying the predetermined voltage to the emitter; detecting, via the detector, an ambient output corresponding to the predetermined voltage.

Clause 34. The method of clause 33, further comprising: adjusting, using the ambient output, the value of the biomarker of the subject.

Clause 35. The method of clause 33, further comprising: detecting the ambient output prior to recording the detector output from the optical sensing device in contact with the subject.

Clause 36. A system for calibration of an optical sensing device, the system comprising: a master optical sensing device including an emitter, a detector, and an optical component coupled to the emitter and the detector, the optical sensing device further including a power source and electronics including a controller; the controller of the master optical sensing device configured to: apply a plurality of voltages to the emitter; detect, via the detector, an output corresponding to each voltage; record each voltage paired with the corresponding output to a baseline dataset; wherein the plurality of voltages includes an initial voltage, a final voltage, and incremental voltages stepped by a voltage increment between the initial voltage and the final voltage; and generate, using the baseline dataset, a master calibration curve.

Clause 37. The system of clause 36, further comprising: wherein the master optical sensing device is operable to transmit data to an external component including a processor; wherein the external component includes the calibration model and is operable to: receive the baseline dataset from the master optical sensing device; generate the master calibration curve using the calibration model; and transmit the master calibration curve to the master optical sensing device.

Clause 38. The system of clause 36, wherein the optical component is an internal reflection element.

Clause 39. The system of clause 36, where the optical component includes at least one of a crystal, a prism, light pipe, a waveguide, a parabolic mirror, a flat mirror, a linear polarizer, or a circular polarizer.

Clause 40. The system of clause 37, further comprising: a secondary optical sensing device including an emitter, a detector, and an optical component coupled to the emitter and the detector, the secondary optical sensing device further including a power source and electronics including a controller; the controller of the secondary optical sensing device configured to: apply the plurality of voltages to the emitter; detect, via the detector, an output corresponding to each voltage; record each voltage paired with the corresponding output to a secondary dataset; generate, using the secondary dataset, an unadjusted calibration curve; receive, from the master optical sensing device or the external component, a calibration model including the master calibration curve; generate a secondary calibration curve using the calibration model.

Clause 41. The system of clause 40, wherein the calibration model is configured to: adjust the unadjusted calibration curve to align with the master calibration curve.

Clause 42. The system of clause 40, wherein the secondary optical sensing device is operable to transmit data to the external component; wherein the external component is operable to: receive, from the secondary optical sensing device, at least one of the secondary dataset or the unadjusted calibration curve; generate the secondary calibration curve; and transmit the secondary calibration curve to the secondary optical sensing device.

Clause 43. The system of clause 42, wherein at least one of the secondary optical sensing device or the external component is configured to: analyze the unadjusted calibration curve to determine a condition state of the secondary optical device.

Clause 44. The system of clause 43, wherein the condition state corresponds to at least one of a damaged condition, a malfunctioning conditioning, a misaligned condition, or a wear condition of the secondary optical device; wherein at least one of the secondary optical sensing device or the external component is configured to: output an indication of the condition state.

Clause 45. The system of clause 40, wherein each of the master optical sensing device and the secondary optical sensing device is operable as a transdermal optical sensing device for monitoring at least one biomarker in a subject, said each of the master and secondary optical sensing devices further comprising: a biomarker correlation curve for the at least one biomarker; said each of the master and secondary optical sensing devices configured to: be positioned in contact with a subject; activate the emitter; record a detector output corresponding to the predetermined operating voltage of the emitter, when positioned in contact with the subject; wherein the biomarker correlation curve correlates the detector output to a value of the at least one biomarker; and determine, using the detector output and the biomarker correlation curve, a value of the biomarker of the subject.

Clause 46. A method of calibrating an optical sensing device of a transdermal optical sensing system, the transdermal optical sensing system operable for monitoring at least one biomarker in a subject, the system including a master optical sensing device and a secondary optical sensing device, the method comprising: generating, using the master optical sensing device, a master calibration curve; generating, using the secondary optical sensing device, an unadjusted calibration curve; generating, using the unadjusted calibration curve and the master calibration curve, a secondary calibration curve; and calibrating the secondary optical sensing device to the master optical sensing device using the secondary calibration curve.

Clause 47. The method of clause 46, wherein the master optical sensing device includes an emitter, a detector, and an optical component coupled to the emitter and the detector, the master optical sensing device further including a power source and electronics including a controller, the method further comprising: generating the master calibration curve by: isolating the optical component from an external environment; applying a plurality of voltages to the emitter; detecting, via the detector, a detector output corresponding to each voltage; recording each voltage paired with the corresponding detector output to a baseline dataset; wherein the plurality of voltages includes an initial voltage, a final voltage, and incremental voltages stepped by a voltage increment between the initial voltage and the final voltage; and generating, using the baseline dataset, the master calibration curve.

Clause 48. The method of clause 47, further comprising: generating, using the master optical sensing device, a biomarker correlation curve for the at least one biomarker; wherein the biomarker correlation curve correlates the detector output of the detector to a value of the at least one biomarker.

Clause 49. The method of clause 48, wherein the secondary optical sensing device includes an emitter, a detector, and an optical component coupled to the emitter and the detector, the secondary optical sensing device further including a power source and electronics including a controller, the method further comprising: generating, using the secondary optical sensing device, the secondary calibration curve by: isolating the optical component from the external environment; applying the plurality of voltages to the emitter; detecting, via the detector, an output corresponding to each of the voltages; recording the outputs to a secondary dataset; generating the unadjusted calibration curve based on the secondary dataset; and adjusting, using a calibration model, the unadjusted calibration curve to align with the master calibration curve.

Clause 50. The method of clause 49, further comprising: receiving the biomarker correlation curve on the secondary optical sensing device; positioning the secondary optical sensing device in contact with a subject; activating the emitter at a predetermined operating voltage; recording a detector output from the secondary optical sensing device in contact with the subject; determining, using the detector output and the biomarker correlation curve, a value of the biomarker of the subject.

Clause 51. The method of clause 50, further comprising: isolating the optical component of the secondary optical sensing device from the external environment; applying the predetermined voltage to the emitter; detecting, via the detector, an ambient output corresponding to the predetermined voltage; and adjusting, using the ambient output, the value of the biomarker of the subject.

Clause 52. The method of clause 51, further comprising: isolating the optical component and detecting the ambient output prior to positioning the secondary optical sensing device in contact with the subject and recording the detector output from the secondary optical sensing device in contact with the subject.

Clause 53. The method of clause 49, further comprising: analyzing the unadjusted calibration curve to determine a condition state of the secondary optical sensing device.

Clause 54. The method of clause 53, wherein the condition state corresponds to at least one of a damaged condition, a malfunctioning conditioning, a misaligned condition, or a wear condition of the secondary optical sensing device; the method further comprising: outputting an indication of the condition state.

Clause 55. The method of clause 53, wherein analyzing the unadjusted calibration curve includes at least one of: comparing the unadjusted calibration curve to the master calibration curve; and comparing the unadjusted calibration curve to the secondary calibration curve.

Clause 56. The method of clause 49, the method further comprising an external component including a processor, wherein the external component is operable to: receive data from the master optical sensing device; generate the master calibration curve; and transmit the master calibration curve to the master optical sensing device.

Clause 57. The method of clause 49, wherein the external component is operable to: receive data from the secondary optical sensing device; generate the secondary calibration curve; and transmit the secondary calibration curve to the master optical sensing device.

The terminology used herein is for the purpose of describing particular embodiments only and is not intended to be limiting of the present disclosure. The terms "about" and/or "substantially" are intended to include the degree of error associated with measurement of the particular quantity based upon the equipment available at the time of filing the application. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

While the present disclosure has been described with reference to an exemplary embodiment or embodiments, it will be understood by those skilled in the art that various changes may be made and equivalents may be substituted for elements thereof without departing from the scope of the present disclosure. In addition, many modifications may be made to adapt a particular situation or material to the teachings of the present disclosure without departing from the essential scope thereof. Therefore, it is intended that the present disclosure not be limited to the particular embodiment disclosed as the best mode contemplated for carrying out this present disclosure, but that the present disclosure will include all embodiments falling within the scope of the claims.

What is claimed is:

1. A method of calibrating an optical sensing device, wherein the optical sensing device includes an emitter, a detector, and an optical component coupled to the emitter and the detector, the optical sensing device further including a power source and electronics including a controller, the method comprising:
   isolating the optical component from an external environment;
   applying a plurality of voltages to the emitter;
   detecting, via the detector, an output corresponding to each voltage;
   recording each voltage paired with the corresponding output to a baseline dataset;
   wherein the plurality of voltages includes an initial voltage, a final voltage, and incremental voltages stepped by a voltage increment between the initial voltage and the final voltage; and
   generating, using the baseline dataset, a calibration curve.

2. The method of claim 1, wherein applying the plurality of voltages to the emitter includes:
   pulsing the emitter at a frequency of 4 Hertz (Hz) between a high power emission state and a low power emission state of the emitter; and
   polling the detector at a frequency of 8 Hertz (Hz).

3. The method of claim 1, wherein the optical component is an internal reflection element.

4. The method of claim 1, wherein the optical sensing device is operable to transmit data to an external component including a processor, the method further comprising:
transmitting, via the optical sensing device, the baseline dataset to the external component;
wherein the external component is operable to:
generate the calibration curve; and
transmit the calibration curve to the optical sensing device;
the method further comprising:
receiving, via the optical sensing device, the calibration curve.

5. The method of claim 1, wherein the optical sensing device is a master optical sensing device and the calibration curve is a master calibration curve, the method further comprising:
providing a secondary optical device including a secondary emitter, a secondary detector, a secondary optical component, a power source and electronics including a secondary controller;
calibrating the secondary optical device by:
isolating the secondary optical component from the external environment;
applying the plurality of voltages to the secondary emitter;
detecting, via the secondary detector, an output corresponding to each of the voltages;
recording the outputs to a secondary dataset;
generating a secondary calibration curve by:
generating an unadjusted calibration curve based on the secondary dataset;
adjusting, using a calibration model, the unadjusted calibration curve to align with the master calibration curve.

6. The method of claim 5, wherein the secondary optical device is operable to transmit data to an external component including a processor, the method further comprising:
transmitting, via the secondary optical device, the secondary dataset to the external component;
wherein the external component is operable to:
generate the secondary calibration curve using the secondary dataset; and
transmit the secondary calibration curve to the secondary optical device;
the method further comprising:
receiving, via the secondary optical device, the secondary calibration curve.

7. The method of claim 5, wherein the calibration model is operable to adjust the unadjusted calibration curve to align with the master calibration curve by performing an adjustment selected from the group consisting of a linear adjustment, a quadratic adjustment, a polynomial adjustment, and a matrix adjustment.

8. The method of claim 5, wherein the calibration model is a machine learning module selected from the group consisting of a binary classification model, a multiclass classification model, and a regression model.

9. The method of claim 5, wherein the calibration model is a supervised machine learning module.

10. The method of claim 5, wherein the calibration model is an unsupervised machine learning module.

11. The method of claim 5, further comprising:
analyzing the unadjusted calibration curve to determine a condition state of the secondary optical device.

12. The method of claim 11, wherein the condition state corresponds to at least one of a damaged condition, a malfunctioning conditioning, a misaligned condition, or a wear condition of the secondary optical device.

13. The method of claim 11, wherein analyzing the unadjusted calibration curve includes at least one of:
comparing the unadjusted calibration curve to the master calibration curve; and
comparing the unadjusted calibration curve to the secondary calibration curve.

14. The method of claim 1, wherein the optical sensing device is operable as a transdermal optical sensing device for monitoring at least one biomarker in a subject, the method further comprising:
generating a biomarker correlation curve for the at least one biomarker;
wherein generating the biomarker correlation curve includes:
for each subject of a plurality of subjects:
recording a detector output from the optical sensing device in contact with the subject;
wherein the detector output corresponds to a predetermined operating voltage of the emitter; and
obtaining a corresponding laboratory value of the at least one biomarker of the subject; and
correlating, using the detector output and the corresponding laboratory value of the at least one biomarker obtained from the plurality of subjects, the detector output to the values of the at least one biomarker;
wherein the biomarker correlation curve correlates the detector output to a value of the at least one biomarker.

15. The method of claim 14, wherein the at least one biomarker includes a first biomarker and a second biomarker, the method further comprising:
generating a first biomarker correlation curve for the first biomarker; and
generating a second biomarker correlation curve for the second biomarker.

16. The method of claim 14, wherein the at least one biomarker includes a combination biomarker defined by a combination of a first biomarker and a second biomarker, the method further comprising:
generating a combination correlation curve for the combination biomarker.

17. The method of claim 14, further comprising:
positioning the optical sensing device in contact with a subject;
activating the emitter at the predetermined operating voltage;
recording a detector output from the optical sensing device in contact with the subject;
determining, using the detector output and the biomarker correlation curve, a value of the biomarker of the subject.

18. The method of claim 17, further comprising:
isolating the optical sensing device from the external environment;
applying the predetermined voltage to the emitter;
detecting, via the detector, an ambient output corresponding to the predetermined voltage.

19. The method of claim 18, further comprising:
adjusting, using the ambient output, the value of the biomarker of the subject.

20. The method of claim 18, further comprising:
detecting the ambient output prior to recording the detector output from the optical sensing device in contact with the subject.

21. A system for calibration of an optical sensing device, the system comprising:
a master optical sensing device including an emitter, a detector, and an optical component coupled to the emitter and the detector, the optical sensing device further including a power source and electronics including a controller;
the controller of the master optical sensing device configured to:
apply a plurality of voltages to the emitter;
detect, via the detector, an output corresponding to each voltage;
record each voltage paired with the corresponding output to a baseline dataset;
wherein the plurality of voltages includes an initial voltage, a final voltage, and incremental voltages stepped by a voltage increment between the initial voltage and the final voltage; and
generate, using the baseline dataset, a master calibration curve.

22. The system of claim 21, further comprising:
wherein the master optical sensing device is operable to transmit data to an external component including a processor;
wherein the external component includes the calibration model and is operable to:
receive the baseline dataset from the master optical sensing device;
generate the master calibration curve using the calibration model; and
transmit the master calibration curve to the master optical sensing device.

23. The system of claim 22, further comprising:
a secondary optical sensing device including an emitter, a detector, and an optical component coupled to the emitter and the detector, the secondary optical sensing device further including a power source and electronics including a controller;
the controller of the secondary optical sensing device configured to:
apply the plurality of voltages to the emitter;
detect, via the detector, an output corresponding to each voltage;
record each voltage paired with the corresponding output to a secondary dataset;
generate, using the secondary dataset, an unadjusted calibration curve;
receive, from the master optical sensing device or the external component, a calibration model including the master calibration curve;
generate a secondary calibration curve using the calibration model.

24. The system of claim 23, wherein the calibration model is configured to:
adjust the unadjusted calibration curve to align with the master calibration curve.

25. The system of claim 23, wherein the secondary optical sensing device is operable to transmit data to the external component;
wherein the external component is operable to:
receive, from the secondary optical sensing device, at least one of the secondary dataset or the unadjusted calibration curve;
generate the secondary calibration curve; and
transmit the secondary calibration curve to the secondary optical sensing device.

26. The system of claim 25, wherein at least one of the secondary optical sensing device or the external component is configured to:
analyze the unadjusted calibration curve to determine a condition state of the secondary optical device.

27. The system of claim 26, wherein the condition state corresponds to at least one of a damaged condition, a malfunctioning conditioning, a misaligned condition, or a wear condition of the secondary optical device;
wherein at least one of the secondary optical sensing device or the external component is configured to:
output an indication of the condition state.

28. The system of claim 23, wherein each of the master optical sensing device and the secondary optical sensing device is operable as a transdermal optical sensing device for monitoring at least one biomarker in a subject, said each of the master and secondary optical sensing devices further comprising:
a biomarker correlation curve for the at least one biomarker;
said each of the master and secondary optical sensing devices configured to:
be positioned in contact with a subject;
activate the emitter;
record a detector output corresponding to the predetermined operating voltage of the emitter, when positioned in contact with the subject;
wherein the biomarker correlation curve correlates the detector output to a value of the at least one biomarker; and
determine, using the detector output and the biomarker correlation curve, a value of the biomarker of the subject.

29. The system of claim 21, wherein the optical component is an internal reflection element.

* * * * *